(12) United States Patent
Smith et al.

(10) Patent No.: US 9,414,591 B2
(45) Date of Patent: *Aug. 16, 2016

(54) CHITOOLIGOSACCHARIDES AND METHODS FOR USE IN ENHANCING CORN GROWTH

(71) Applicant: NOVOZYMES BIOAG A/S, Bagsvaerd (DK)

(72) Inventors: R. Stewart Smith, Pewaukee, WI (US); Ahsan Habib, Roanoke, VA (US)

(73) Assignee: NOVOZYMES BIOAG A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 14/709,742

(22) Filed: May 12, 2015

(65) Prior Publication Data

US 2015/0237856 A1 Aug. 27, 2015

Related U.S. Application Data

(63) Continuation of application No. 13/625,409, filed on Sep. 24, 2012, now Pat. No. 9,055,747.

(60) Provisional application No. 61/538,354, filed on Sep. 23, 2011.

(51) Int. Cl.
*A01N 43/16* (2006.01)
*A01N 63/04* (2006.01)
*A01N 25/00* (2006.01)

(52) U.S. Cl.
CPC ............. *A01N 43/16* (2013.01); *A01N 25/00* (2013.01); *A01N 63/04* (2013.01)

(58) Field of Classification Search
CPC ....................... A01N 43/16; A01N 25/00
See application file for complete search history.

(56) References Cited

U.S. PATENT DOCUMENTS

| | | | |
|---|---|---|---|
| 4,536,207 A | 8/1985 | McCandliss | |
| 4,804,750 A | 2/1989 | Nishimura | |
| 4,812,159 A | 3/1989 | Freepons | |
| 4,886,541 A | 12/1989 | Hadwiger | |
| 4,940,840 A | 7/1990 | Suslow | |
| 4,964,894 A | 10/1990 | Freepons | |
| 4,978,381 A | 12/1990 | Hadwiger | |
| 5,026,417 A | 6/1991 | Kucey | |
| 5,057,141 A | 10/1991 | Rodriguez-Kabana | |
| 5,104,437 A | 4/1992 | Hadwiger | |
| 5,141,745 A | 8/1992 | Rolfe | |
| 5,175,149 A | 12/1992 | Stacey | |
| 5,321,011 A | 6/1994 | Stacey | |
| 5,374,627 A | 12/1994 | Ito | |
| 5,454,464 A | 10/1995 | Yamamoto | |
| 5,536,155 A | 7/1996 | Futaki | |
| 5,549,718 A | 8/1996 | Lerouge | |
| 5,554,445 A | 9/1996 | Struszczyk | |
| 5,586,411 A | 12/1996 | Gleddie | |
| 5,628,810 A | 5/1997 | Dugast | |
| 5,646,018 A | 7/1997 | Broughton | |
| 5,696,098 A | 12/1997 | Muraki | |
| 5,702,752 A | 12/1997 | Gugger | |
| 5,705,634 A | 1/1998 | Bredehorst | |
| 5,720,793 A | 2/1998 | Kato | |
| 5,726,123 A | 3/1998 | Heinsohn | |
| 5,733,851 A | 3/1998 | Villanueva | |
| 5,830,459 A | 11/1998 | Cuero | |
| 5,922,316 A | 7/1999 | Smith | |
| 5,965,545 A | 10/1999 | Ben-Shalom | |
| 5,990,291 A | 11/1999 | Waggle | |
| 6,060,429 A | 5/2000 | Ben-Shalom | |
| 6,146,668 A | 11/2000 | Kelly | |
| 6,167,652 B1 | 1/2001 | Heinsohn | |
| 6,193,988 B1 | 2/2001 | Stoner | |
| 6,197,942 B1 | 3/2001 | Muraki | |
| 6,200,929 B1 | 3/2001 | Horibe | |
| 6,242,381 B1 | 6/2001 | van der Krieken | |
| 6,258,749 B1 | 7/2001 | Nonomura | |
| 6,306,835 B1 | 10/2001 | Daly | |
| 6,352,727 B1 | 3/2002 | Takahashi | |
| 6,407,040 B1 | 6/2002 | Nichols | |
| 6,413,910 B1 | 7/2002 | Vasiljevich | |
| 6,524,998 B1 | 2/2003 | Kloepper | |
| 6,589,352 B1 | 7/2003 | Yudovsky | |

(Continued)

FOREIGN PATENT DOCUMENTS

| | | |
|---|---|---|
| CA | 2202024 A1 | 10/1998 |
| CN | 101092315 A | 12/2007 |

(Continued)

OTHER PUBLICATIONS van der Holst et al. 2001. Current Opinions in Structural Biology 11, 608-616.
Robina et al. 2002 Tetrahedron 58, 521-530.
Samain et al. 1999, Journal of Biotechnology 72, 33-47.
Samain et al 1997, Carbohydrate Research 302, 35-42.
Cottaz et al 2005, Metabolic Engineering 7, 311-317.
Dumon et al 2006, ChemBioChem 7, 359-365.
Denaire et al 1996, Annu. Rev. Biochem. 65, 503-535.
Khan et al 2002, Photosynthetica 40(4), 621-624.
Jung et al 2007, Carbohydrate Polymers 67, 256-259.
Yoshikawa et al 1993, Plant Cell Physiol. 34(8), 1163-1173.
Hamel et al 2010, Planta 232, 787-806.

(Continued)

*Primary Examiner* — Ali Soroush
*Assistant Examiner* — Genevieve S Alley
(74) *Attorney, Agent, or Firm* — Adam Rucker

(57) ABSTRACT

Disclosed are methods of enhancing growth of corn plants, comprising treating corn seed or the corn plant that germinates from the seed with an effective amount of at least one chitooligosaccharide, wherein upon harvesting the corn plant exhibits at least one of increased plant yield measured in terms of bushels/acre, increased root number, increased root length, increased root mass, increased root volume and increased leaf area, compared to untreated corn plants or corn plants harvested from untreated corn seed.

28 Claims, 9 Drawing Sheets

(56) References Cited

U.S. PATENT DOCUMENTS

| | | | |
|---|---|---|---|
| 6,589,942 | B1 | 7/2003 | Ben-Shalom |
| 6,630,459 | B2 | 10/2003 | Vournakis |
| 6,649,566 | B2 | 11/2003 | Doostdar |
| 6,849,576 | B2 | 2/2005 | Suzuki |
| 6,878,819 | B1 | 4/2005 | Natunen |
| 6,933,380 | B2 | 8/2005 | Huang |
| 6,979,664 | B1 | 12/2005 | Smith |
| 7,098,324 | B2 | 8/2006 | Haigler |
| 7,205,450 | B2 | 4/2007 | Cook |
| 7,250,068 | B1 | 7/2007 | Smith |
| 7,262,151 | B2 | 8/2007 | Smith |
| 7,485,718 | B2 | 2/2009 | Sabesan |
| 7,521,212 | B1 | 4/2009 | Samain |
| 7,576,213 | B2 | 8/2009 | Flematti |
| 7,619,076 | B2 | 11/2009 | Beau |
| 7,637,980 | B2 | 12/2009 | Smith |
| 7,670,820 | B2 | 3/2010 | Shaw |
| 8,008,544 | B2 | 8/2011 | Block |
| 8,357,631 | B2 | 1/2013 | Smith |
| 2002/0000540 | A1 | 1/2002 | Smither-Kopperl |
| 2005/0187107 | A1 | 8/2005 | Smith |
| 2006/0277632 | A1 | 12/2006 | Carr |
| 2007/0027032 | A1 | 2/2007 | Chen |
| 2007/0105815 | A1 | 5/2007 | Vournakis |
| 2007/0238872 | A1 | 10/2007 | Sabesan |
| 2008/0057093 | A1 | 3/2008 | Wan |
| 2008/0072494 | A1 | 3/2008 | Stoner |
| 2008/0172763 | A1 | 7/2008 | Jensen |
| 2008/0248953 | A1 | 10/2008 | Smith |
| 2008/0269055 | A1 | 10/2008 | Bastiaans |
| 2009/0305895 | A1 | 12/2009 | McIver |
| 2010/0031388 | A1 | 2/2010 | Tirichine |
| 2010/0048404 | A1 | 2/2010 | Hungenberg |
| 2010/0087369 | A1 | 4/2010 | Cutsem |
| 2010/0093537 | A1 | 4/2010 | Smith |
| 2010/0099560 | A1 | 4/2010 | Hnatowich |
| 2010/0113278 | A1 | 5/2010 | Suty-Heinze |
| 2011/0301032 | A1 | 12/2011 | Denarie |
| 2012/0077674 | A1 | 3/2012 | Cargeeg |
| 2012/0322659 | A1 | 12/2012 | Smith |
| 2013/0061645 | A1 | 3/2013 | Smith |
| 2013/0109567 | A1 | 5/2013 | Smith |

FOREIGN PATENT DOCUMENTS

| | | |
|---|---|---|
| CN | 101248797 A | 8/2008 |
| CN | 101543230 A | 9/2009 |
| CN | 101601410 A | 12/2009 |
| FR | 2941591 A1 | 3/2009 |
| JP | 8003010 A2 | 1/1996 |
| WO | 89/07395 A1 | 8/1989 |
| WO | 92/17591 A1 | 10/1992 |
| WO | 98/34464 A2 | 8/1998 |
| WO | 00/04778 A1 | 2/2000 |
| WO | 01/26465 A1 | 4/2001 |
| WO | 03/077654 A1 | 9/2003 |
| WO | 2004/093542 A1 | 11/2004 |
| WO | 2005/062899 A1 | 7/2005 |
| WO | 2005/063784 A1 | 7/2005 |
| WO | 2005/087005 A1 | 9/2005 |
| WO | 2007/006318 A2 | 1/2007 |
| WO | 2008/085958 A1 | 7/2008 |
| WO | 2009/049747 A2 | 4/2009 |
| WO | 2010/049751 A1 | 5/2010 |
| WO | 2010/125065 A2 | 11/2010 |

OTHER PUBLICATIONS

Okada et al 2002, Plant Cell Physiol 43(5), 505-512.
Muller et al 2000, Plant Physiology 124, 733-739.
Prome et al 1998, Pure & Appl. Chem. 70(1), 55-60.
Newsmart webpage re COS, www.glucosamine-chitosan.com (2005).
Darvill et al 1992, Glycobiology 2(3), 181-198.
Cote et al 1994, Plant Molecular Biology 26, 1379-1411.
Kasprezewska 2003, Cellular & Molecular Biology Letters 8, 809-824.
Cote et al 1995, Physiologiz Plantarium 93, 401-410.
Halford 2010, "Smoke Signals", Chemical & Engineering News 88(15), 1-3.
D'Haeze et al 2002, Glycobiology 12(6), 79R-105R.
Demont-Caulet et al 1999, Plant Physiology 120, 83-92.
Maillet et al 2011, Nature 469, 58-64.
Macchiavelli et al 2004, Journal of Experimental Botany 55(408), 2635-2640.
Spaink 2000, Annu. Rev. Micriobiol 54, 257-288.
Pochanavanich et al 2002, Letters in Applied Microbiology 35, 17-21.
Shaw et al 2006, Environmental Microbiology 8(11), 1867-1880.
Ralston et al 2005, Plant Physiology 137, 1375-1388.
Wakelin et al 2004, Biol Fertil Soils 40, 36-43.
Diaz et al 2000, Molecular Plant-Microbe Interactions 13(3), 268-276.
Hungria et al 1997, Soil Biol. Biochem. 29(516), 819-830.
Friesen et al 2005, Appl Microbiol Biotechnol 68, 397-404.
Ferguson et al 2003, J Plant Growth Regul 22, 47-72.
Collinge et al 1993, The Plant Journal 3(1), 31-40.
Leibovitch et al 2001, J Agronomy & Crop Science 187, 281-292.
Pederson presentation Iowa State University "Soybean Growth and Development" (2009).
Prithiviraj et al 2003, Planta 216, 437-445.
Staehelin et al 1994, Proc. Natl. Acad. Sci. USA 91, 2196-2200.
Cytryn et al, 2007, J Bacteriology, 189(19), 6751-6762.
Deaker et al., 2007, Soil Biology & Biochemistry 39 573-580.
LePrince et al, 2010, Plant Science 179 554-564.
Mabood et al, 2006, Field Crops Research, 95 412-419.
Mary et al, 1994, Soil Biol Biochem 26(9), 1125-1132.
Radwan et al, 2007, Intl J Phytoremediation 9, 475-486.
Streeter, 2003, J Appl Microbiol 95, 484-491.
Sugawara et al, 2010, Appl Environ Microbiol 76(4), 1071-1081.
Supanjani et al, 2006 Plant Physiology and Biochemistry, 44 866-872.
Zahran., 2001, Journal of Biotechnology, 91 143-153.
Yong et al, 2011, Fine Chem 28(5), 479-483, Abstract only.
Jian-ping et al, 2011, J Anhui Agric Sci 39(1), 88-89, Abstract only.
Halford et al, 2010, Chem Eng New 88 (15), 37-38.
Maj et al, 2009, J Chem Ecol 35, 479-487—(Spec).
Noreen et al. 2003, Func Plant Biol 30, 1219-1232.
Hamid et al. 2013, J. Pharm. Bioallied Sci Jan.-Mar. 5(1), 21-29.
Nishizawa et al. 1999, Plant Molecular Biology 39, 907-914.
Ramonell et al. 2005, Plant Physiology 138, 1027-1036.
Wan et al. 2008, The Plant Cell 20, 471-481.
Zhang et al. 2002, MPMI 15(9), 963-970.

CHITOOLIGOSACCHARIDES AND METHODS FOR USE IN ENHANCING CORN GROWTH

CROSS-REFERENCE TO RELATED APPLICATIONS

This application is a continuation of U.S. application Ser. No. 13/625,409 filed on Sep. 24, 2012, now allowed, which claims priority or the benefit under 35 U.S.C. 119 of U.S. provisional application No. 61/538,354 filed Sep. 23, 2011, the contents of which are fully incorporated herein by reference.

BACKGROUND OF THE INVENTION

The symbiosis between the gram-negative soil bacteria, Rhizobiaceae and Bradyrhizobiaceae, and legumes such as soybean, is well documented. The biochemical basis for these relationships includes an exchange of molecular signaling, wherein the plant-to-bacteria signal compounds include flavones, isoflavones and flavanones, and the bacteria-to-plant signal compounds, which include the end products of the expression of the bradyrhizobial and rhizobial nod genes, known as lipo-chitooligosaccharides (LCOs). The symbiosis between these bacteria and the legumes enables the legume to fix atmospheric nitrogen for plant growth, thus obviating a need for nitrogen fertilizers. Since nitrogen fertilizers can significantly increase the cost of crops and are associated with a number of polluting effects, the agricultural industry continues its efforts to exploit this biological relationship and develop new agents and methods for improving plant yield without increasing the use of nitrogen-based fertilizers.

U.S. Pat. No. 6,979,664 teaches a method for enhancing seed germination or seedling emergence of a plant crop, comprising the steps of providing a composition that comprises an effective amount of at least one lipo-chitooligosaccharide and an agriculturally suitable carrier and applying the composition in the immediate vicinity of a seed or seedling in an effective amount for enhancing seed germination of seedling emergence in comparison to an untreated seed or seedling.

Further development on this concept is taught in WO 2005/062899, directed to combinations of at least one plant inducer, namely an LCO, in combination with a fungicide, insecticide, or combination thereof, to enhance a plant characteristic such as plant stand, growth, vigor and/or yield. The compositions and methods are taught to be applicable to both legumes and non-legumes, and may be used to treat a seed (just prior to planting), seedling, root or plant.

Similarly, WO 2008/085958 teaches compositions for enhancing plant growth and crop yield in both legumes and non-legumes, and which contain LCOs in combination with another active agent such as a chitin or chitosan, a flavonoid compound, or an herbicide, and which can be applied to seeds and/or plants concomitantly or sequentially. As in the case of the '899 Publication, the '958 Publication teaches treatment of seeds just prior to planting.

More recently, Halford, "Smoke Signals," in Chem. Eng. News (Apr. 12, 2010), at pages 37-38, reports that karrikins or butenolides which are contained in smoke act as growth stimulants and spur seed germination after a forest fire, and can invigorate seeds such as corn, tomatoes, lettuce and onions that had been stored. These molecules are the subject of U.S. Pat. No. 7,576,213.

There is, however, still a need for systems for improving or enhancing plant growth.

BRIEF SUMMARY OF THE INVENTION

A first aspect of the present invention is directed to a method of enhancing growth of corn plants, comprising a) treating (e.g., applying to) corn seed or a corn plant that germinates from the seed, with an effective amount of at least one chitooligosaccharide (CO), wherein upon harvesting the corn plant exhibits at least one of increased plant yield measured in terms of bushels/acre, increased root number, increased root length, increased root mass, increased root volume and increased leaf area, compared to untreated corn plants or plants harvested from untreated corn seed.

In some embodiments, at least two CO's are used. In some embodiments, treatment of the corn seed includes direct application of the at least one CO onto the seed, which may then be planted or stored for a period of time prior to planting. Treatment of the corn seed may also include indirect treatment such as by introducing the at least one CO into the soil (known in the art as in-furrow application). In yet other embodiments, the at least one CO may be applied to the corn plant that germinates from the seed, e.g., via foliar spray. The methods may further include use of other agronomically beneficial agents, such as micronutrients, fatty acids and derivatives thereof, plant signal molecules ((other than CO's), such as lipo-chitooligosaccharides, chitinous compounds (other than COs), flavonoids, jasmonic acid and derivatives thereof, linoleic acid and derivatives thereof, linolenic acid and derivatives thereof, and karrikins and derivatives thereof), herbicides, fungicides and insecticides, and phosphate-solubilizing microorganisms.

As demonstrated by the working examples, which summarize experiments conducted in both the greenhouse and in the field, the results achieved by the methods of the present invention show that application of at least one CO to corn seed or a corn plant that germinates from a seed, results in enhanced plant growth. These results are believed to be unexpected, particularly from the standpoint that COs were known to be involved in system acquired resistance (SAR) but not necessarily involved in the direct enhancement of plant growth. The results described herein show that in some cases, the inventive methods achieved a substantially equal effect or in some other cases, outperformed the enhancement of plant growth achieved by an LCO. The results obtained from the greenhouse experiments are particularly significant in this regard, in that they were conducted in substantially disease-free conditions.

DETAILED DESCRIPTION

Chitooligosaccharides

COs are known in the art as β-1-4 linked N-acetyl glucosamine structures identified as chitin oligomers, also as N-acetylchitooligosaccharides. CO's have unique and different side chain decorations which make them different from chitin molecules [$(C_8H_{13}NO_5)_n$, CAS No. 1398-61-4], and chitosan molecules [$(C_5H_{11}NO_4)_n$, CAS No. 9012-76-4]. See, e.g., Hamel, et al., Planta 232:787-806 (2010) (e.g., FIG. 1 which shows structures of chitin, chitosan, Nod factors (LCO's), and the corresponding CO's (which would lack the 18C, 16C, or 20C acyl group)). The CO's of the present invention are also relatively water-soluble compared to chitin and chitosan, and in some embodiments, as described hereinbelow, are pentameric. Representative literature describing the structure and production of COs that may be suitable for use in the present invention is as follows: Muller, et al., Plant Physiol. 124:733-9 (2000)(e.g., FIG. 1 therein); Van der Holst, et al., Current Opinion in Structural Biology, 11:608-616 (2001) (e.g., FIG. 1 therein); Robina, et al., Tetrahedron 58:521-530 (2002); D'Haeze, et al., Glycobiol. 12(6):79R-105R (2002); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (9/21/2000); and Demont-Caulet, et al., Plant Physiol. 120(1):83-92 (1999).

CO's differ from LCO's in terms of structure mainly in that they lack the pendant fatty acid chain. Rhizobia-derived CO's, and non-naturally occurring synthetic derivatives thereof, that may be useful in the practice of the present invention may be represented by the following formula:

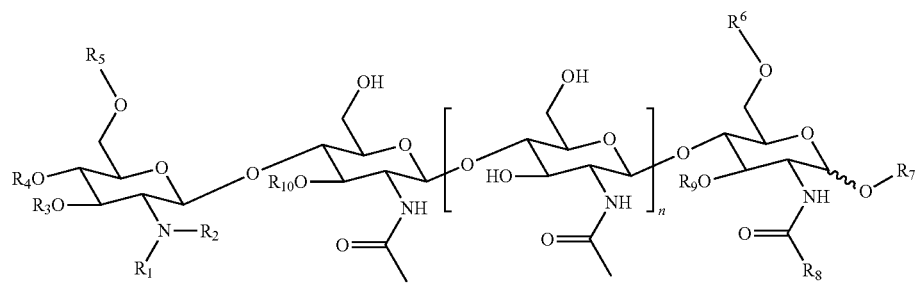

wherein $R_1$ and $R_2$ each independently represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc, and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3. The structures of corresponding Rhizobial LCO's are described in D'Haeze, et al., supra.

Figure 1A:
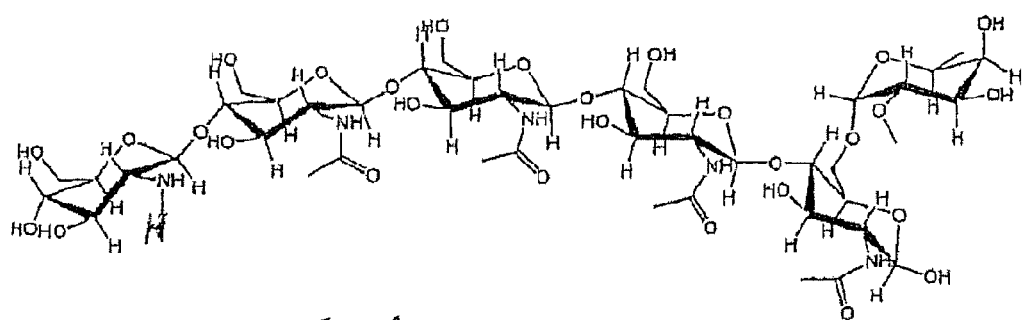
FIGS. 1a and 2a show the chemical structures of chitooligosaccharide compounds (CO's) useful in the practice of the present invention.
Figure 1B:
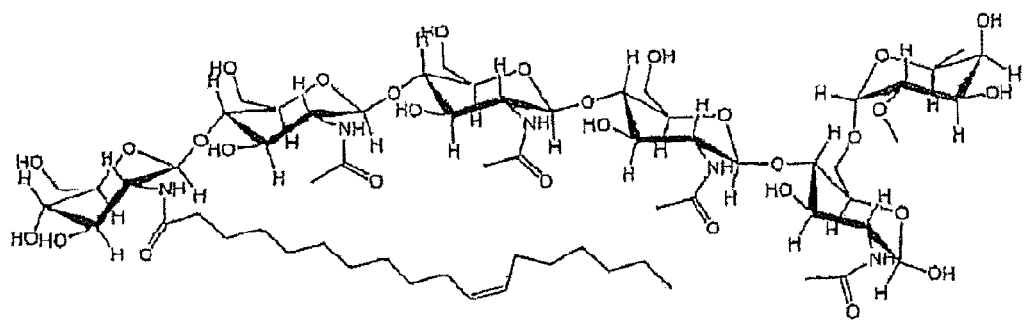
FIGS. 1b and 2b show the chemical structures of the lipo-chitooligosaccharide compounds (LCO's) that correspond to the CO's in FIGS. 1a and 2a, and which are also useful in the practice of the present invention.
Figure 2A:
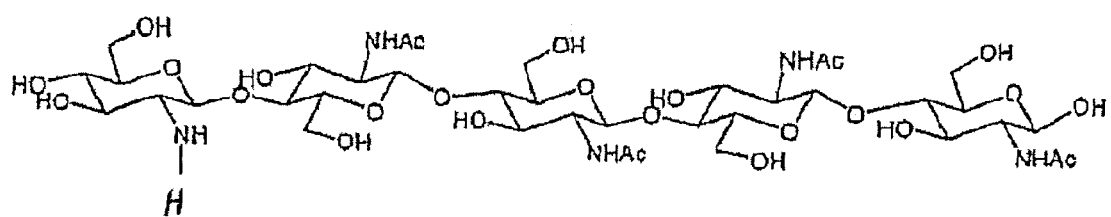
Figure 2B:
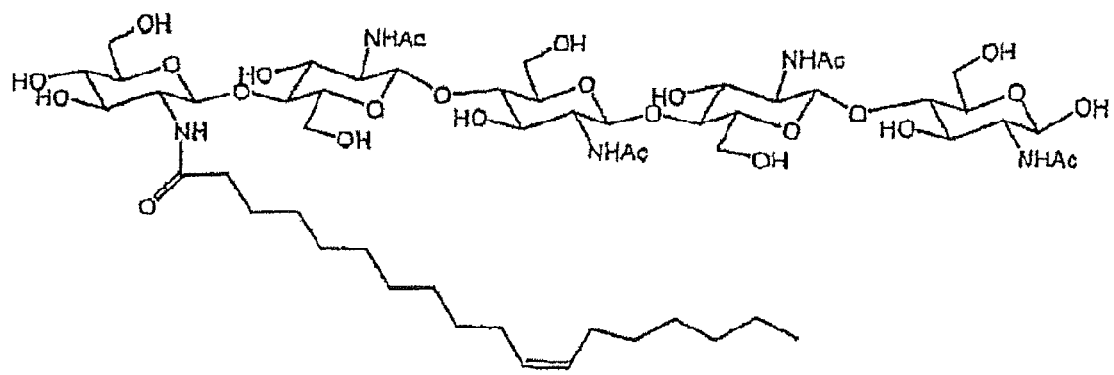

Two CO's suitable for use in the present invention are illustrated in FIGS. 1a and 2a. They correspond to LCO's produced by *Bradyrhizobium japonicum* and *Rhizobium leguminosarum biovar viciae* respectively, which interact symbiotically with soybean and pea, respectively, but lack the fatty acid chains. The corresponding LCO's produced by these rhizobia (and which are also useful in the practice of the present invention) are illustrated in FIGS. 1b and 2b.

Figure 3A:
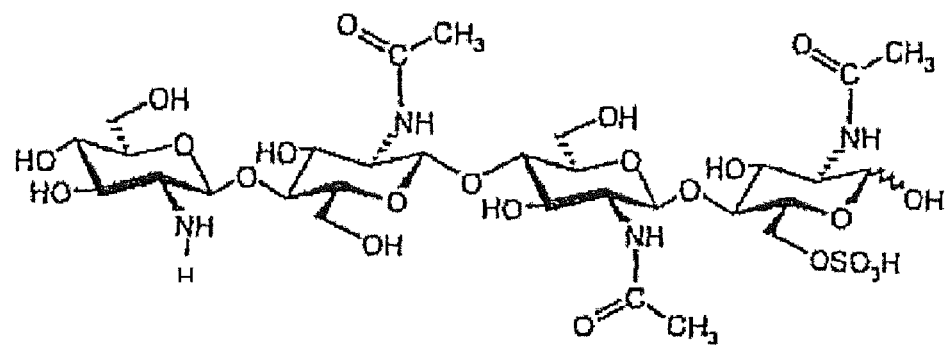
FIGS. 3a and 4a show the chemical structures of other CO's useful in the practice of the present invention.
Figure 3B:
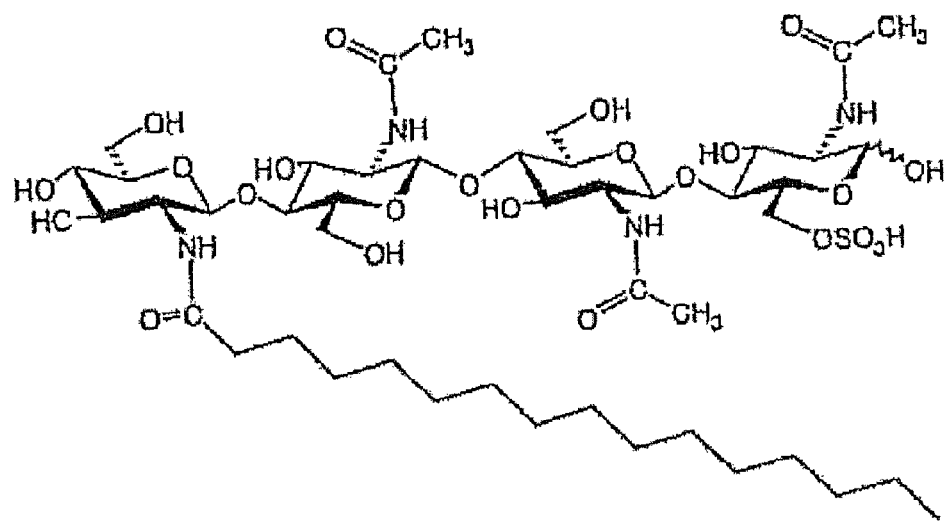
FIGS. 3b and 4b show the chemical structures of the Myc-factors that correspond to the CO's in FIGS. 3a and 3b, and which are also useful in the practice of the present invention.
Figure 4A:
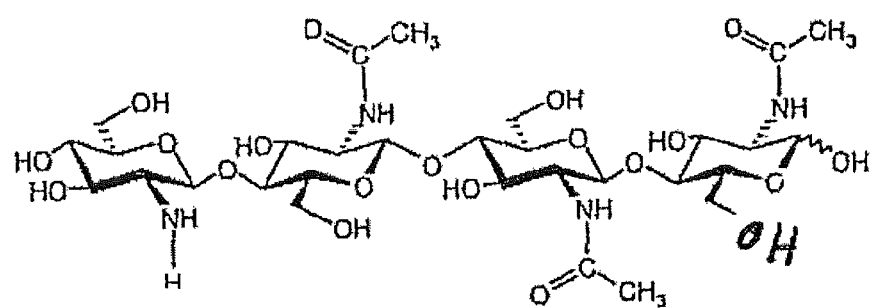
Figure 4B:
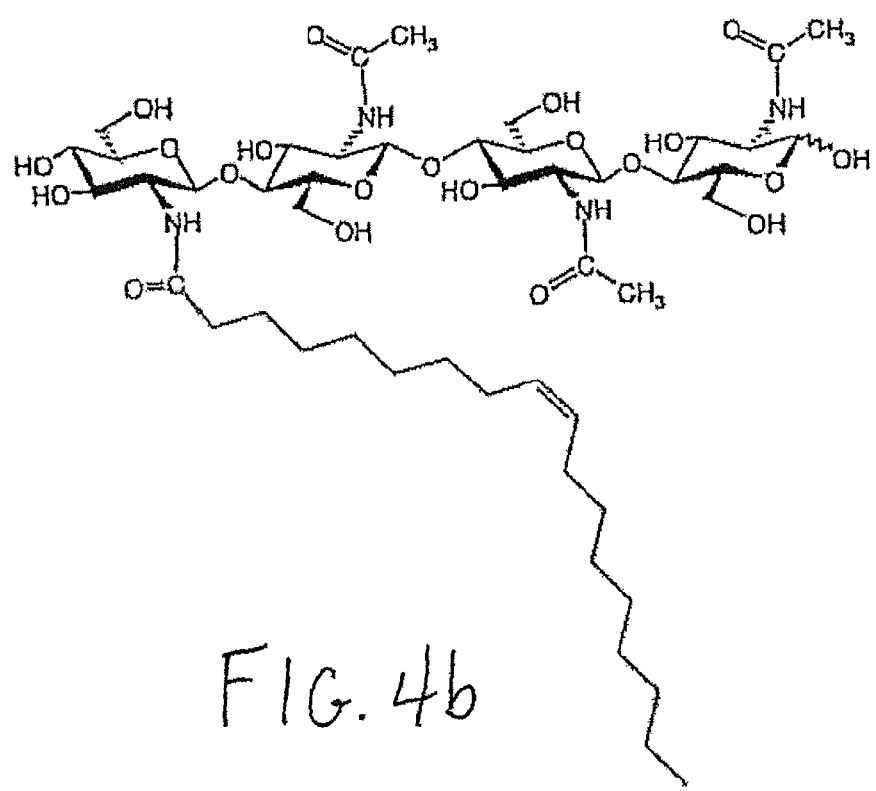

The structures of yet other CO's that may be suitable for use in the practice of the present invention are easily derivable from LCOs obtained (i.e., isolated and/or purified) from a mycorrhizal fungi, such as fungi of the group Glomerocycota, e.g., *Glomus intraradices*. See, e.g., WO 2010/049751 and Maillet, et al., Nature 469:58-63 (2011) (the LCOs described therein also referred to as "Myc factors"). Representative mycorrhizal fungi-derived CO's are represented by the following structure:

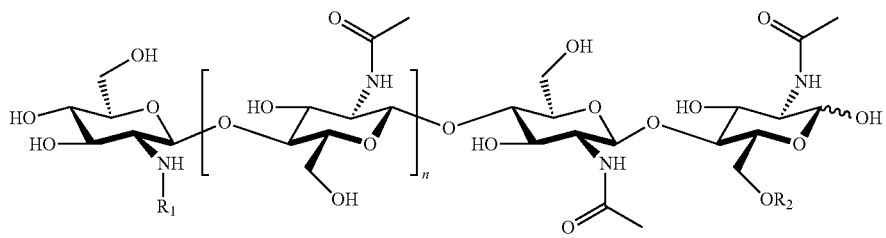

wherein n=1 or 2; $R_1$ represents hydrogen or methyl; and $R_2$ represents hydrogen or $SO_3H$. Two other CO's suitable for use in the present invention, one of which is sulfated, and the other being non-sulfated, are illustrated in FIGS. 3a and 4a respectively. They correspond to two different LCO's produced by the mycorrhizal fungi *Glomas intraradices* which are illustrated in FIGS. 3b and 4b (and which are also useful in the practice of the present invention).

The COs may be synthetic or recombinant. Methods for preparation of synthetic CO's are described, for example, in Robina, supra., Methods for producing recombinant CO's e.g., using *E. coli* as a host, are known in the art. See, e.g., Dumon, et al., ChemBioChem 7:359-65 (2006), Samain, et al., Carbohydrate Res. 302:35-42 (1997); Cottaz, et al., Meth. Eng. 7(4):311-7 (2005) and Samain, et al., J. Biotechnol. 72:33-47 (1999) (e.g., FIG. 1 therein which shows structures of CO's that can be made recombinantly in *E. coli* harboring different combinations of genes nodBCHL). For purposes of the present invention, the at least one CO is structurally distinct from chitins, chitosans, and other chitooligosaccharides made enzymatically using chitin as a starting material.

For the purposes of the present invention, in embodiments in which the at least one CO is recombinant, the at least one recombinant CO is at least 60% pure, e.g., at least 60% pure, at least 65% pure, at least 70% pure, at least 75% pure, at least 80% pure, at least 85% pure, at least 90% pure, at least 91% pure, at least 92% pure, at least 93% pure, at least 94% pure, at least 95% pure, at least 96% pure, at least 97% pure, at least 98% pure, at least 99% pure, up to 100% pure.

Corn seeds may be treated with the at least one CO in several ways such as spraying or dripping. Spray and drip treatment may be conducted by formulating an effective amount of the at least one CO in an agriculturally acceptable carrier, typically aqueous in nature, and spraying or dripping the composition onto seed via a continuous treating system (which is calibrated to apply treatment at a predefined rate in proportion to the continuous flow of seed), such as a drum-type of treater. These methods advantageously employ relatively small volumes of carrier so as to allow for relatively fast drying of the treated seed. In this fashion, large volumes of seed can be efficiently treated. Batch systems, in which a predetermined batch size of seed and signal molecule compositions are delivered into a mixer, may also be employed. Systems and apparatus for performing these processes are commercially available from numerous suppliers, e.g., Bayer CropScience (Gustafson).

In another embodiment, the treatment entails coating corn seeds with the at least one CO. One such process involves coating the inside wall of a round container with the composition, adding seeds, then rotating the container to cause the seeds to contact the wall and the composition, a process known in the art as "container coating". Seeds can be coated by combinations of coating methods. Soaking typically entails use of an aqueous solution containing the plant growth enhancing agent. For example, seeds can be soaked for about 1 minute to about 24 hours (e.g., for at least 1 min, 5 min, 10 min, 20 min, 40 min, 80 min, 3 hr, 6 hr, 12 hr, 24 hr). Some types of seeds (e.g., soybean seeds) tend to be sensitive to moisture. Thus, soaking such seeds for an extended period of time may not be desirable, in which case the soaking is typically carried out for about 1 minute to about 20 minutes.

In those embodiments that entail storage of corn seed after application of the at least one CO, adherence of the CO to the seed over any portion of time of the storage period is not critical. Without intending to be bound by any particular theory of operation, Applicants believe that even to the extent that the treating may not cause the plant signal molecule to remain in contact with the seed surface after treatment and during any part of storage, the CO may achieve its intended effect by a phenomenon known as seed memory or seed perception. See, Macchiavelli, et al., J. Exp. Bot. 55(408): 1635-40 (2004). Applicants also believe that following treatment the CO diffuses toward the young developing radicle and activates symbiotic and developmental genes which results in a change in the root architecture of the plant. Notwithstanding, to the extent desirable, the compositions containing the CO may further contain a sticking or coating agent. For aesthetic purposes, the compositions may further contain a coating polymer and/or a colorant.

The amount of the at least one CO is effective to enhance growth such that upon harvesting the corn plant exhibits at least one of increased plant yield measured in terms of bushels/acre, increased root number, increased root length, increased root mass, increased root volume and increased leaf area, compared to untreated corn plants or corn plants harvested from untreated corn seed (with either active). The effective amount of the at least one CO used to treat the corn seed, expressed in units of concentration, generally ranges from about $10^{-5}$ to about $10^{-14}$ M (molar concentration), and in some embodiments, from about $10^{-5}$ to about $10^{-11}$ M, and in some other embodiments from about $10^{-7}$ to about $10^{-5}$ M. Expressed in units of weight, the effective amount generally ranges from about 1 to about 400 μg/hundred weight (cwt) seed, and in some embodiments from about 2 to about 70 μg/cwt, and in some other embodiments, from about 2.5 to about 3.0 μg/cwt seed.

For purposes of treatment of corn seed indirectly, i.e., in-furrow treatment, the effective amount of the at least one CO generally ranges from about 1 μg/acre to about 70 μg/acre, and in some embodiments, from about 50 μg/acre to about 60 μg/acre. For purposes of application to the plants, the effective amount of the CO generally ranges from about 1 μg/acre to about 30 μg/acre, and in some embodiments, from about 11 μg/acre to about 20 μg/acre.

Corn seed may be treated with the at least one CO just prior to or at the time of planting. Treatment at the time of planting may include direct application to the seed as described above, or in some other embodiments, by introducing the actives into the soil, known in the art as in-furrow treatment. In those embodiments that entail treatment of seed followed by storage, the seed may be then packaged, e.g., in 50-lb or 100-lb bags, or bulk bags or containers, in accordance with standard techniques. The seed may be stored for at least 1, 2, 3, 4, 5, 6, 7, 8, 9, 10, 11, or 12 months, and even longer, e.g., 13, 14, 15, 16, 17, 18, 19, 20, 21, 22, 23, 24, 25, 26, 27, 28, 29, 30, 31, 32, 33, 34, 35, 36 months, or even longer, under appropriate storage conditions which are known in the art.

Other Agronomically Beneficial Agents

The present invention may further include treatment of the corn seed or the corn plants that germinate from the seed with at least one agriculturally/agronomically beneficial agent. As used herein and in the art, the term "agriculturally or agronomically beneficial" refers to agents that when applied to corn seeds or corn plants results in enhancement (which may be statistically significant) of corn plant characteristics such as plant stand, growth (e.g., as defined in connection with CO's), or vigor in comparison to non-treated corn seeds or corn plants. These agents may be formulated together with the at least one CO or applied to the seed or plant via a separate formulation. Representative examples of such agents that may be useful in the practice of the present invention include micronutrients (e.g., vitamins and trace minerals), fatty acids and derivatives thereof, plant signal molecules (other than CO's), herbicides, fungicides and insecticides, and phosphate-solubilizing microorganisms.

Micronutrients

Representative vitamins that may be useful in the practice of the present invention include calcium pantothenate, folic acid, biotin, and vitamin C. Representative examples of trace minerals that may be useful in the practice of the present invention include boron, chlorine, manganese, iron, zinc, copper, molybdenum, nickel, selenium and sodium.

The amount of the at least one micronutrient used to treat the corn seed, expressed in units of concentration, generally ranges from 10 ppm to 100 ppm, and in some embodiments, from about 2 ppm to about 100 ppm. Expressed in units of weight, the effective amount generally ranges in one embodiment from about 180 µg to about 9 mg/hundred weight (cwt) seed, and in some embodiments from about 4 µg to about 200 µg/plant when applied on foliage. In other words, for purposes of treatment of seed the effective amount of the at least one micronutrient generally ranges from 30 µg/acre to about 1.5 mg/acre, and in some embodiments, from about 120 mg/acre to about 6 g/acre when applied foliarly.

Fatty Acids

Representative fatty acids that may be useful in the practice of the present invention include the fatty acids that are substituents on naturally occurring LCO's, such as stearic and palmitic acids. Other fatty acids that may be useful include saturated C12-18 fatty acids which (aside from palmitic and stearic acids) include lauric acid, and myristic acid, and unsaturated C12-18 fatty acids such as myristoleic acid, palmitoleic acid, sapienic acid, oleic acid, elaidic acid, vaccenic acid, linoleic acid, linolenic acid, and linoelaidic acid. Linoleic acid and linolenic acid are produced in the course of the biosynthesis of jasmonic acid (which as described below, is also an agronomically beneficial agent for purposes of the present invention). Linoleic acid and linoleic acid (and their derivatives) are reported to be inducers of nod gene expression or LCO production by rhizobacteria. See, e.g., Mabood, Fazli, "Linoleic and linolenic acid induce the expression of nod genes in *Bradyrhizobium japonicum*," USDA 3, May 17, 2001.

Useful derivatives of fatty acids that may be useful in the practice of the present invention include esters, amides, glycosides and salts. Representative esters are compounds in which the carboxyl group of the fatty acid, e.g., linoleic acid and linolenic acid, has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of the fatty acid, e.g., linoleic acid and linolenic acid, has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of fatty acids, e.g., linoleic acid and linolenic acid, include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of the fatty acid with a solution of the base. The salt may be precipitated from solution and be collected by filtration or may be recovered by other means such as by evaporation of the solvent.

The amounts of the fatty acid or derivative thereof used to treat the corn seed or corn plants are typically between about 10% to about 30%, and in some embodiments about 25% of the amount of the at least one CO.

Plant Signal Molecules

The present invention may also include treatment of the corn seed or corn plant with a plant signal molecule other than a CO. For purposes of the present invention, the term "plant signal molecule", which may be used interchangeably with "plant growth-enhancing agent" broadly refers to any agent, both naturally occurring in plants or microbes, and synthetic (and which may be non-naturally occurring) that directly or indirectly activates a plant biochemical pathway, resulting in increased corn plant growth, measureable at least in terms of at least one of increased yield measured in terms of bushels/acre, increased root number, increased root length, increased root mass, increased root volume and increased leaf area, compared to untreated corn plants or corn plants harvested from untreated corn seed. Representative examples of plant signal molecules that may be useful in the practice of the present invention include lipo-chitooligosaccharides; chitinous compounds (other than COs); flavonoids; jasmonic acid, linoleic acid and linolenic acid and their derivatives (supra); and karrikins and their derivatives.

Lipo-chitooligosaccharide compounds (LCO's), also known in the art as symbiotic Nod signals or Nod factors, consist of an oligosaccharide backbone of β-I,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. See, e.g., Denarie, et al., Ann. Rev. Biochem. 65:503-35 (1996), Hamel, et al., supra., Prome, et al., Pure & Appl. Chem. 70(1):55-60 (1998). An example of an LCO is presented below as formula I

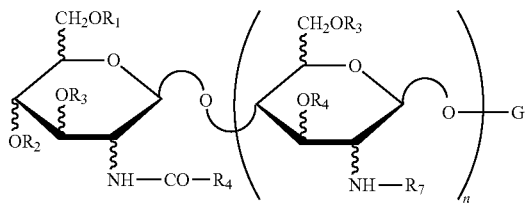

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO$—, $C_xH_yCO$— where x is an integer between 0 and 17, and y is an integer between 1 and 35, or any other acyl group such as for example a carbamoyl, $R_4$ represents a mono-, di- or triunsaturated aliphatic chain containing at least 12 carbon atoms, and n is an integer between 1 and 4.

LCOs may be obtained (isolated and/or purified) from bacteria such as Rhizobia, e.g., *Rhizobium* sp., *Bradyrhizobium* sp., *Sinorhizobium* sp. and *Azorhizobium* sp. LCO structure is characteristic for each such bacterial species, and each strain may produce multiple LCO's with different structures. For example, specific LCOs from *S. meliloti* have also been described in U.S. Pat. No. 5,549,718 as having the formula II:

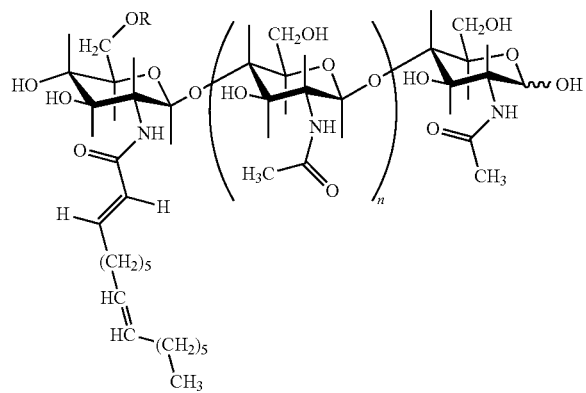

in which R represents H or $CH_3CO$— and n is equal to 2 or 3.

Even more specific LCOs include NodRM, NodRM-1, NodRM-3. When acetylated (the $R=CH_3CO$—), they become AcNodRM-1, and AcNodRM-3, respectively (U.S. Pat. No. 5,545,718).

LCOs from *Bradyrhizobium japonicum* are described in U.S. Pat. Nos. 5,175,149 and 5,321,011. Broadly, they are pentasaccharide phytohormones comprising methylfucose. A number of these *B. japonicum*-derived LCOs are described: BjNod-V ($C_{18:1}$); BjNod-V ($A_C$, $C_{18:1}$), BjNod-V ($C_{16:1}$); and BjNod-V ($A_C$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

LCO's used in embodiments of the invention may be obtained (i.e., isolated and/or purified) from bacterial strains that produce LCO's, such as strains of *Azorhizobium, Bradyrhizobium* (including *B. japonicum*), *Mesorhizobium, Rhizobium* (including *R. leguminosarum*), *Sinorhizobium* (including *S. meliloti*), and bacterial strains genetically engineered to produce LCO's.

LCO's are the primary determinants of host specificity in legume symbiosis (Diaz, et al., Mol. Plant-Microbe Interactions 13:268-276 (2000)). Thus, within the legume family, specific genera and species of rhizobia develop a symbiotic nitrogen-fixing relationship with a specific legume host. These plant-host/bacteria combinations are described in Hungria, et al., Soil Biol. Biochem. 29:819-830 (1997), Examples of these bacteria/legume symbiotic partnerships include *S. meliloti*/alfalfa and sweet clover; *R. leguminosarum* biovar *viciae*/peas and lentils; *R. leguminosarum* biovar *phaseolil*-beans; *Bradyrhizobium japonicum*/soybeans; and *R. leguminosarum* biovar *trifolii*/red clover. *Hungria* also lists the effective flavonoid Nod gene inducers of the rhizobial species, and the specific LCO structures that are produced by the different rhizobial species. However, LCO specificity is only required to establish nodulation in legumes. In the practice of the present invention, use of a given LCO is not limited to treatment of seed of its symbiotic legume partner, in order to achieve increased plant yield measured in terms of bushels/acre, increased root number, increased root length, increased root mass, increased root volume and increased leaf area, compared to plants harvested from untreated seed, or compared to plants harvested from seed treated with the signal molecule just prior to or within a week or less of planting.

Thus, by way of further examples, LCO's and non-naturally occurring derivatives thereof that may be useful in the practice of the present invention are represented by the following formula:

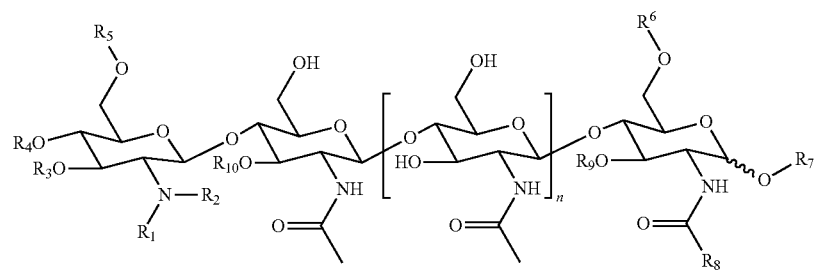

wherein R₁ represents C14:0, 3OH—C14:0, iso-C15:0, C16: 0, 3-OH—C16:0, iso-C15:0, C16:1, C16:2, C16:3, iso-C17: 0, iso-C17:1, C18:0, 30H-C18:0, 018:0/3-OH, C18:1, OH—C18:1, C18:2, C18:3, C18:4, C19:1 carbamoyl, C20:0, C20:1, 3-OH—C20:1, C20:1/3-OH, C20:2, C20:3, C22:1, and C18-26(ω-1)-OH (which according to D'Haeze, et al., supra, includes C18, C20, C22, C24 and C26 hydroxylated species and C16:1Δ9, C16:2 (Δ2,9) and C16:3 (Δ2,4,9)); R₂ represents hydrogen or methyl; R₃ represents hydrogen, acetyl or carbamoyl; R₄ represents hydrogen, acetyl or carbamoyl; R₅ represents hydrogen, acetyl or carbamoyl; R₆ represents hydrogen, arabinosyl, fucosyl, acetyl, sulfate ester, 3-0-S-2-0-MeFuc, 2-0-MeFuc, and 4-0-AcFuc; R₇ represents hydrogen, mannosyl or glycerol; R₈ represents hydrogen, methyl, or —CH₂OH; R₉ represents hydrogen, arabinosyl, or fucosyl; R₁₀ represents hydrogen, acetyl or fucosyl; and n represents 0, 1, 2 or 3. The structures of the naturally occurring Rhizobial LCO's embraced by this structure are described in D'Haeze, et al., supra.

By way of even further additional examples, an LCO obtained from *B. japonicum*, illustrated in FIG. 1b, may be used to treat leguminous seed other than soybean and non-leguminous seed such as corn. As another example, the LCO obtainable from *R. leguminosarum* illustrated in FIG. 2b (designated LCO-V (C18:1), SP104) can be used to treat leguminous seed other than pea and non-legumes too.

Also encompassed by the present invention is use of LCOs obtained (i.e., isolated and/or purified) from a mycorrhizal fungi, such as fungi of the group Glomerocycota, e.g., *Glomus intraradices*. The structures of representative LCOs obtained from these fungi are described in WO 2010/049751 and WO 2010/049751 (the LCOs described therein also referred to as "Myc factors"). Representative mycorrhizal fungi-derived CO's and non-naturally occurring derivatives thereof are represented by the following structure:

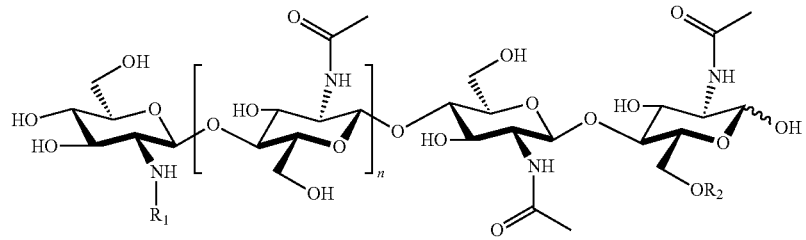

wherein n=1 or 2; R₁ represents C16, C16:0, C16:1, C16:2, C18:0, C18:1Δ9Z or C18:1Δ11Z; and R₂ represents hydrogen or SO₃H. In some embodiments, the LCO's are produced by the mycorrhizal fungi which are illustrated in FIGS. 3b and 4b.

Further encompassed by the present invention is use of synthetic LCO compounds, such as those described in WO 2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present invention) for the construction of LCOs may also be synthesized by genetically engineered organisms, e.g., as described in Samain, et al., Carbohydrate Res. 302:35-42 (1997); Cottaz, et al., Meth. Eng. 7(4):311-7 (2005) and Samain, et al., J. Biotechnol. 72:33-47 (1999)(e.g., FIG. 1 therein which shows structures of LCO's that can be made recombinantly in *E. coli* harboring different combinations of genes nodBCHL).

LCO's may be utilized in various forms of purity and may be used alone or in the form of a culture of LCO-producing bacteria or fungi. For example, OPTIMIZE® (commercially available from Novozymes BioAg Limited) contains a culture of *B. japonicum* that produces an LCO (LCO-V(C18:1, MeFuc), MOR116) that is illustrated in FIG. 1b Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage. Chitooligosaccharides (COs) as described above, may be used as starting materials for the production of synthetic LCOs. For the purposes of the present invention, recombinant LCO's are at least 60% pure, e.g., at least 60% pure, at least 65% pure, at least 70% pure, at least 75% pure, at least 80% pure, at least 85% pure, at least 90% pure, at least 91% pure, at least 92% pure, at least 93% pure, at least 94% pure, at least 95% pure, at least 96% pure, at least 97% pure, at least 98% pure, at least 99% pure, up to 100% pure.

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4, 5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), and chitosan, (IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2 (hydroxymethyl)oxane-3,4-diol). These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965, 545 (preparation from crab shells and hydrolysis of commercial chitosan). See, also, Jung, et al., Carbohydrate Polymers 67:256-59 (2007); Khan, et al., Photosynthetica 40(4):621-4 (2002). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 OkD; and high molecular weight chitosan of up to 70 OkD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include chalcones, anthocyanidins, coumarins, flavones, flavanols, flavonols, flavanones, and isoflavones. See, Jain, et al., J. Plant Biochem. & Biotechnol. 11:1-10 (2002); Shaw, et al., Environmental Microbiol. 11:1867-80 (2006).

Representative flavonoids that may be useful in the practice of the present invention include genistein, daidzein, formononetin, naringenin, hesperetin, luteolin, and apigenin. Flavonoid compounds are commercially available, e.g., from Natland International Corp., Research Triangle Park, NC; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston, et al., Plant Physiology 137:1375-88 (2005).

Jasmonic acid (JA, [1R-[1α,2β(Z)]]-3-oxo-2-(pentenyl) cyclopentaneacetic acid) and its derivatives (which include linoleic acid and linolenic acid (which are described above in connection with fatty acids and their derivatives), may be used in the practice of the present invention. Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibbrella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Like linoleic acid and linolenic acid, jasmonates (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001.

Useful derivatives of jasmonic acid that may be useful in the practice of the present invention include esters, amides, glycosides and salts. Representative esters are compounds in which the carboxyl group of jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikins are vinylogous 4H-pyrones e.g., 2H-furo[2,3-c]pyran-2-ones including derivatives and analogues thereof. Examples of these compounds are represented by the following structure:

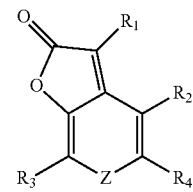

wherein; Z is O, S or NR$_5$; R$_1$, R$_2$, R$_3$, and R$_4$ are each independently H, alkyl, alkenyl, alkynyl, phenyl, benzyl, hydroxy, hydroxyalkyl, alkoxy, phenyloxy, benzyloxy, CN, COR$_6$, COOR=, halogen, NR$_6$R$_7$, or NO$_2$; and R$_5$, R$_6$, and R$_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present invention include the following: 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R4=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH$_3$), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H), 3,6-dimethylfuro[2,3-c]pyridin-2(6H)-one (where Z=N——CH$_3$, R$_1$=CH$_3$, R$_2$, R$_3$, R$_4$=H). See, U.S. Pat. No. 7,576,213. These molecules are also known as karrikins. See, Halford, supra.

The amount of the at least one plant signal molecule used to treat the corn seed, expressed in units of concentration, generally ranges from about $10^{-5}$ to about $10^{-14}$ M (molar concentration), and in some embodiments, from about $10^{-5}$ to about $10^{11}$ M, and in some other embodiments from about $10^{-7}$ to about $10^{-8}$ M. Expressed in units of weight, the effective amount generally ranges from about 1 to about 400 µg/hundred weight (cwt) seed, and in some embodiments from about 2 to about 70 µg/cwt, and in some other embodiments, from about 2.5 to about 3.0 µg/cwt seed.

For purposes of treatment of corn seed indirectly, i.e., in-furrow treatment, the effective amount of the at least one plant signal molecule generally ranges from 1 µg/acre to about 70 µg/acre, and in some embodiments, from about 50 µg/acre to about 60 µg/acre. For purposes of application to the corn plants, the effective amount of the at least one plant signal molecule generally ranges from 1 µg/acre to about 30 µg/acre, and in some embodiments, from about 11 µg/acre to about 20 µg/acre.

Herbicides, Fungicides and Insecticides

Suitable herbicides include bentazon, acifluorfen, chlorimuron, lactofen, clomazone, fluazifop, glufosinate, glyphosate, sethoxydim, imazethapyr, imazamox, fomesafe, flumiclorac, imazaquin, and clethodim. Commercial products containing each of these compounds are readily available. Herbicide concentration in the composition will generally correspond to the labeled use rate for a particular herbicide.

A "fungicide" as used herein and in the art, is an agent that kills or inhibits fungal growth. As used herein, a fungicide "exhibits activity against" a particular species of fungi if treatment with the fungicide results in killing or growth inhibition of a fungal population (e.g., in the soil) relative to an untreated population. Effective fungicides in accordance with the invention will suitably exhibit activity against a broad range of pathogens, including but not limited to *Phytophthora, Rhizoctonia, Fusarium, Pythium, Phomopsis* or *Selerotinia* and *Phakopsora* and combinations thereof.

Commercial fungicides may be suitable for use in the present invention. Suitable commercially available fungicides include PROTÉGÉ, RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAPTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides are most suitably used in accordance with the manufacturer's instructions at the recommended concentrations.

As used herein, an insecticide "exhibits activity against" a particular species of insect if treatment with the insecticide results in killing or inhibition of an insect population relative to an untreated population. Effective insecticides in accordance with the invention will suitably exhibit activity against a broad range of insects including, but not limited to, wireworms, cutworms, grubs, corn rootworm, seed corn maggots, flea beetles, chinch bugs, aphids, leaf beetles, and stink bugs.

Commercial insecticides may be suitable for use in the present invention. Suitable commercially-available insecticides include CRUISER (Syngenta, Wilmington, Del.), GAUCHO and PONCHO (Gustafson, Plano, Tex.). Active ingredients in these and other commercial insecticides include thiamethoxam, clothianidin, and imidacloprid. Commercial insecticides are most suitably used in accordance with the manufacturer's instructions at the recommended concentrations.

Phosphate Solubilizing Microorganisms, Diazotrophs (Rhizobial Inoculants), and/or Mycorrhizal Fungi The present invention may further include treatment of the corn seed with a phosphate solubilizing microorganism. As used herein, "phosphate solubilizing microorganism" is a microorganism that is able to increase the amount of phosphorous available for a plant. Phosphate solubilizing microorganisms include fungal and bacterial strains. In embodiment, the phosphate solubilizing microorganism is a spore forming microorganism.

Non-limiting examples of phosphate solubilizing microorganisms include species from a genus selected from the group consisting of *Acinetobacter, Arthrobacter, Arthrobotrys, Aspergillus, Azospirillum, Bacillus, Burkholderia, Candida Chryseomonas, Enterobacter, Eupenicillium, Exiguobacterium, Klebsiella, Kluyvera, Microbacterium, Mucor, Paecilomyces, Paenibacillus, Penicillium, Pseudomonas, Serratia, Stenotrophomonas, Streptomyces, Streptosporangium, Swaminathania, Thiobacillus, Torulospora, Vibrio, Xanthobacter*, and *Xanthomonas*.

Non-limiting examples of phosphate solubilizing microorganisms are selected from the group consisting *Acinetobacter calcoaceticus, Acinetobacter* sp, *Arthrobacter* sp., *Arthrobotrys oligospora, Aspergillus niger, Aspergillus* sp., *Azospirillum halopraeferans, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter* sp., *Enterobacter taylorae, Eupenicillium parvum, Exiguobacterium* sp., *Klebsiella* sp., *Kluyvera cryocrescens, Microbacterium* sp., *Mucor ramosissimus, Paecilomyces hepialid, Paecilomyces marquandii, Paenibacillus macerans, Paenibacillus mucilaginosus, Pantoea aglomerans, Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Streptomyces* sp., *Streptosporangium* sp., *Swaminathania salitolerans, Thiobacillus ferrooxidans, Torulospora globosa, Vibrio proteolyticus, Xanthobacter agilis*, and *Xanthomonas campestris*

In a particular embodiment, the phosphate solubilizing microorganism is a strain of the fungus *Penicillium*. Strains of the fungus *Penicillium* that may be useful in the practice of the present invention include *P. bilaiae* (formerly known as *P. bilaii), P. albidum, P. aurantiogriseum, P. chrysogenum, P. citreonigrum, P. citrinum, P. digitatum, P. frequentas, P. fuscum, P. gaestrivorus, P. glabrum, P. griseofulvum, P. implicatum, P. janthinellum, P. lilacinum, P. minioluteum, P. montanense, P. nigricans, P. oxalicum, P. pinetorum, P. pinophilum, P. purpurogenum, P. radicans, P. radicum, P. raistrickii, P. rugulosum, P. simplicissimum, P. solitum, P. variabile, P. velutinum, P. viridicatum, P. glaucum, P. fussiporus*, and *P. expansum*.

In one particular embodiment, the *Penicillium* species is *P. bilaiae*. In another particular embodiment the *P. bilaiae* strains are selected from the group consisting of ATCC 20851, NRRL 50169, ATCC 22348, ATCC 18309, NRRL 50162 (Wakelin, et al., 2004. Biol Fertil Soils 40:36-43). In another particular embodiment the *Penicillium* species is *P. gaestrivorus*, e.g., NRRL 50170 (see, Wakelin, supra.).

In some embodiments, more than one phosphate solubilizing microorganism is used, such as, at least two, at least three, at least four, at least five, at least 6, including any combination of the *Acinetobacter, Arthrobacter, Arthrobotrys, Aspergillus, Azospirillum, Bacillus, Burkholderia, Candida Chryseomo-* nas, *Enterobacter, Eupenicillium, Exiguobacterium, Klebsiella, Kluyvera, Microbacterium, Mucor, Paecilomyces, Paenibacillus, Penicillium, Pseudomonas, Serratia, Stenotrophomonas, Streptomyces, Streptosporangium, Swaminathania, Thiobacillus, Torulospora, Vibrio, Xanthobacter,* and *Xanthomonas*, including one species selected from the following group: *Acinetobacter calcoaceticus, Acinetobacter* sp, *Arthrobacter* sp., *Arthrobotrys oligospora, Aspergillus niger, Aspergillus* sp., *Azospirillum halopraeferans, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter* sp., *Enterobacter taylorae, Eupenicillium parvum, Exiguobacterium* sp., *Klebsiella* sp., *Kluyvera cryocrescens, Microbacterium* sp., *Mucor ramosissimus, Paecilomyces hepialid, Paecilomyces marquandii, Paenibacillus macerans, Paenibacillus mucilaginosus, Pantoea aglomerans, Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Streptomyces* sp., *Streptosporangium* sp., *Swaminathania salitolerans, Thiobacillus ferrooxidans, Torulospora globosa, Vibrio proteolyticus, Xanthobacter agilis*, and *Xanthomonas campestris*

In some embodiments, two different strains of the same species may also be combined, for example, at least two different strains of *Penicillium* are used. The use of a combination of at least two different *Penicillium* strains has the following advantages. When applied to soil already containing insoluble (or sparingly soluble) phosphates, the use of the combined fungal strains will result in an increase in the amount of phosphorus available for plant uptake compared to the use of only one *Penicillium* strain. This in turn may result in an increase in phosphate uptake and/or an increase in yield of plants grown in the soil compared to use of individual strains alone. The combination of strains also enables insoluble rock phosphates to be used as an effective fertilizer for soils which have inadequate amounts of available phosphorus. Thus, in some embodiments, one strain of *P. bilaiae* and one strain of *P. gaestrivorus* are used. In other embodiments, the two strains are NRRL 50169 and NRRL 50162. In further embodiments, the at least two strains are NRRL 50169 and NRRL 50170. In yet further embodiments, the at least two strains are NRRL 50162 and NRRL 50170.

The phosphate solubilizing microorganisms may be prepared using any suitable method known to the person skilled in the art, such as, solid state or liquid fermentation using a suitable carbon source. The phosphate solubilizing microorganism is preferably prepared in the form of a stable spore.

In an embodiment, the phosphate solubilizing microorganism is a *Penicillium* fungus. The *Penicillium* fungus according to the invention can be grown using solid state or liquid fermentation and a suitable carbon source. *Penicillium* isolates may be grown using any suitable method known to the person skilled in the art. For example, the fungus may be cultured on a solid growth medium such as potato dextrose agar or malt extract agar, or in flasks containing suitable liquid media such as Czapek-Dox medium or potato dextrose broth. These culture methods may be used in the preparation of an inoculum of *Penicillium* spp. for treating (e.g., coating) seeds and/or application to an agronomically acceptable carrier to be applied to soil. The term "inoculum" as used in this specification is intended to mean any form of phosphate solubilizing microorganism, fungus cells, mycelium or spores, bacterial cells or bacterial spores, which is capable of propagating on or in the soil when the conditions of temperature, moisture, etc., are favorable for fungal growth.

Solid state production of *Penicillium* spores may be achieved by inoculating a solid medium such as a peat or vermiculite-based substrate, or grains including, but not limited to, oats, wheat, barley, or rice. The sterilized medium (achieved through autoclaving or irradiation) is inoculated with a spore suspension ($1 \times 10^2$-$1 \times 10^7$ cfu/ml) of the appropriate *Penicillium* spp. and the moisture adjusted to 20 to 50%, depending on the substrate. The material is incubated for 2 to 8 weeks at room temperature. The spores may also be produced by liquid fermentation (Cunningham et al., 1990. Can J Bot. 68:2270-2274). Liquid production may be achieved by cultivating the fungus in any suitable media, such as potato dextrose broth or sucrose yeast extract media, under appropriate pH and temperature conditions that may be determined in accordance with standard procedures in the art.

The resulting material may be used directly, or the spores may be harvested, concentrated by centrifugation, formulated, and then dried using air drying, freeze drying, or fluid bed drying techniques (Friesen, et al., 2005, Appl. Microbiol. Biotechnol. 68:397-404) to produce a wettable powder. The wettable powder is then suspended in water, applied to the surface of seeds, and allowed to dry prior to planting. The wettable powder may be used in conjunction with other seed treatments, such as, but not limited to, chemical seed treatments, carriers (e.g., talc, clay, kaolin, silica gel, kaolinite) or polymers (e.g., methylcellulose, polyvinylpyrrolidone). Alternatively, a spore suspension of the appropriate *Penicillium* spp. may be applied to a suitable soil-compatible carrier (e.g., peat-based powder or granule) to appropriate final moisture content. The material may be incubated at room temperature, typically for about 1 day to about 8 weeks, prior to use.

Aside from the ingredients used to cultivate the phosphate solubilizing microorganism, including, e.g., ingredients referenced above in the cultivation of *Penicillium*, the phosphate solubilizing microorganism may be formulated using other agronomically acceptable carriers. As used herein in connection with "carrier", the term "agronomically acceptable" refers to any material which can be used to deliver the actives to a corn seed, soil or corn plant, and preferably which carrier can be added (to the seed, soil or plant) without having an adverse effect on plant growth, soil structure, soil drainage or the like. Suitable carriers comprise, but are not limited to, wheat chaff, bran, ground wheat straw, peat-based powders or granules, gypsum-based granules, and clays (e.g., kaolin, bentonite, montmorillonite). When spores are added to the soil a granular formulation will be preferable. Formulations as liquid, peat, or wettable powder will be suitable for coating of corn seeds. When used to coat corn seeds, the material can be mixed with water, applied to the seeds and allowed to dry. Example of yet other carriers include moistened bran, dried, sieved and applied to seeds prior coated with an adhesive, e.g., gum arabic. In embodiments that entail formulation of the actives in a single composition, the agronomically acceptable carrier may be aqueous.

The amount of the at least one phosphate solubilizing microorganism varies depending on the type of soil, the amounts of the source of phosphorus and/or micronutrients present in the soil or added thereto, etc. A suitable amount can be found by simple trial and error experiments for each particular case. Normally, for Penicillium, for example, the application amount falls into the range of 0.001-1.0 Kg fungal spores and mycelium (fresh weight) per hectare, or $10^2$-$10^6$ colony forming units (cfu) per seed (when coated seeds are used), or on a granular carrier applying between $1 \times 10^6$ and $1 \times 10^{11}$ colony forming units per hectare. The fungal cells in the form of e.g., spores and the carrier can be added to a seed row of the soil at the root level or can be used to coat seeds prior to planting.

In embodiments, for example, that entail use of at least two strains of a phosphate solubilizing microorganism, such as, two strains of *Penicillium,* commercial fertilizers may be added to the soil instead of (or even as well as) natural rock phosphate. The source of phosphorous may contain a source of phosphorous native to the soil. In other embodiments, the source of phosphorous may be added to the soil. In one embodiment the source is rock phosphate. In another embodiment the source is a manufactured fertilizer. Commercially available manufactured phosphate fertilizers are of many types. Some common ones are those containing monoammonium phosphate (MAP), triple super phosphate (TSP), diammonium phosphate, ordinary superphosphate and ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In a further embodiment, the source or phosphorus is organic. An organic fertilizer refers to a soil amendment derived from natural sources that guarantees, at least, the minimum percentages of nitrogen, phosphate, and potash. Examples include plant and animal by-products, rock powders, seaweed, inoculants, and conditioners. Specific representative examples include bone meal, meat meal, animal manure, compost, sewage sludge, or guano.

Other fertilizers, such as nitrogen sources, or other soil amendments may of course also be added to the soil at approximately the same time as the phosphate solubilizing microorganism or at other times, so long as the other materials are not toxic to the fungus.

The invention will now be described in terms of the following non-limiting examples. Unless indicated to the contrary, water was used as the control (indicated as "control" or "CHK").

EXAMPLES

Greenhouse Experiments

Example 1

Corn Seed Treatment

Two seed treatment experiments using only Pea LCO, Pea CO and the CO mixtures obtained from chitosan by enzymatic process (structurally distinct from the Pea CO, and also referred to in the examples as the "China CO") were performed in greenhouse. Hybrid corn seeds (92L90, Peterson Farm, USA) were treated with treatment solution (10-8 M) at the rate of 3 fl oz/100 lbs of seed. Seeds were planted in plastic pots containing 1:1 Sand:Perlite mixture. Seeds were allowed to grow for about 3-4 weeks and then they were harvested and their dry weight measured.

Figure 5:
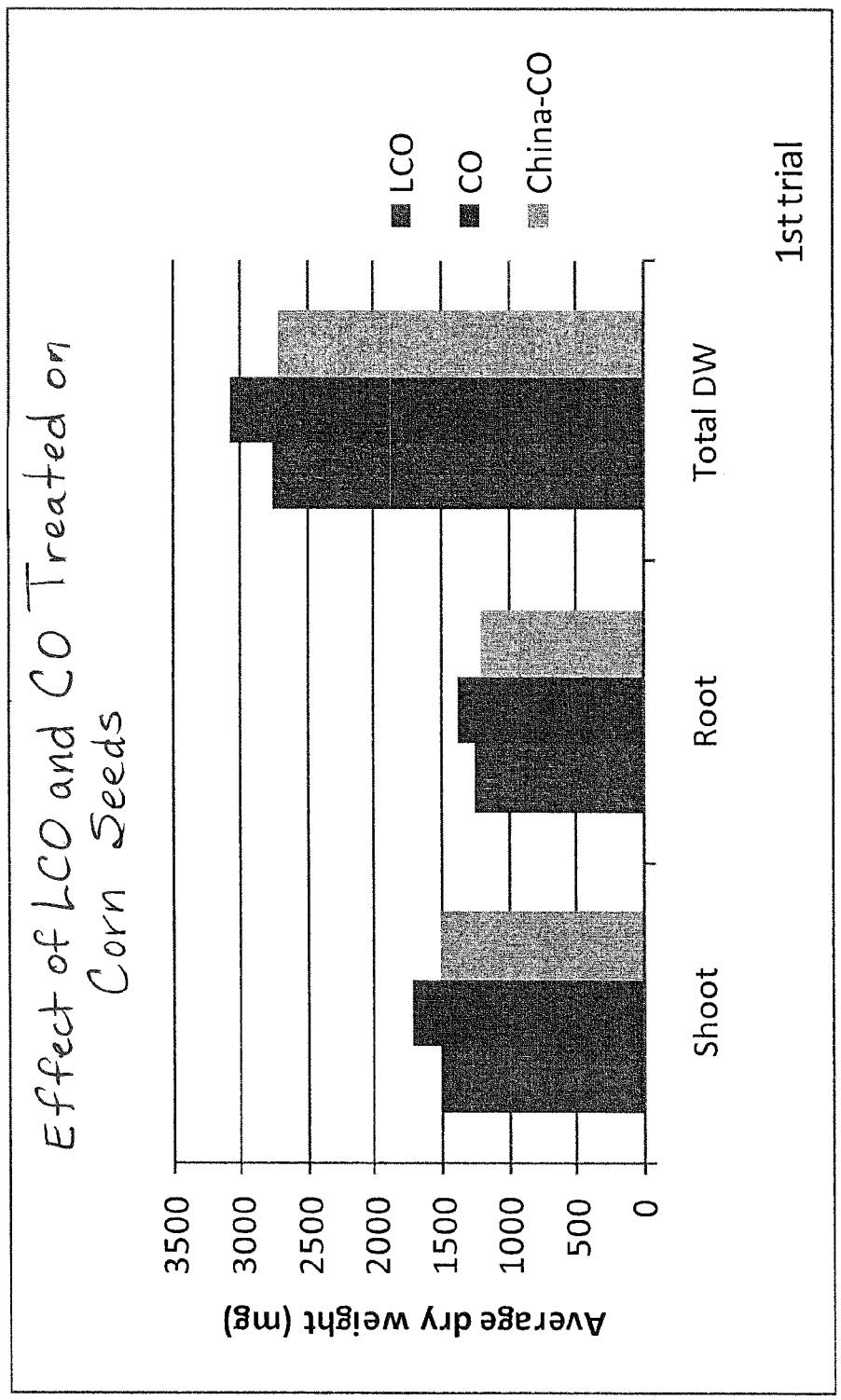
FIGS. 5 (trial 1) and 6 (trial 2) are bar graphs that show the effect of the CO illustrated in FIG. 2a, compared to the LCO illustrated in FIG. 2b, and a mixture of (non-inventive) chitinous compounds produced by chitinase, treated on corn seed, expressed in terms of average dry weight of shoots, roots and total dry weight (combined dry weight of shoots and roots).
Figure 6:
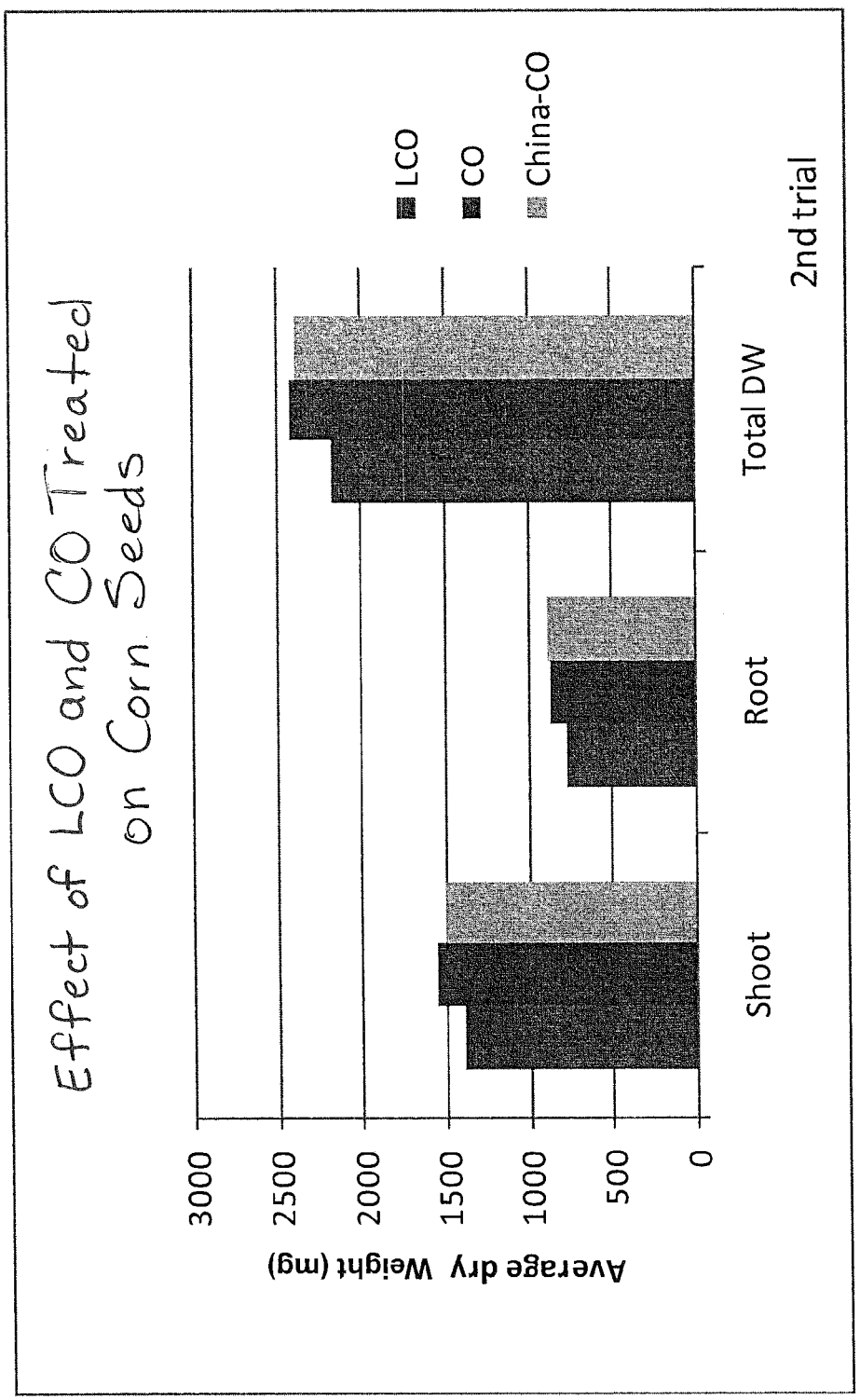

Results obtained from both experiments indicated that inventive (pea CO) showed greater shoot, root and total biomass increase over non-inventive and comparable LCO. For the first trial CO had 11.84% dry weight increase over LCO (FIG. 5). In the second trial, CO had 12.63% dry weight-increase over LCO (FIG. 6). China CO, which may also be considered as a substitute source of pea CO, also demonstrated increased plant dry weight increase as compared to non-inventive LCO

Example 2

Corn Seed Germination in Petriplates

Corn seeds were plated in petriplates containing 5 ml of treatment solution on a filter paper. Corn seeds were placed on moist filter paper for germination. Similarly, wheat seeds (spring wheat) were placed in petriplates. Corn seeds were observed for germinated seedlings 5 days after plating. Roots were harvested and their length measured by WinRhizo system.

Figure 7:
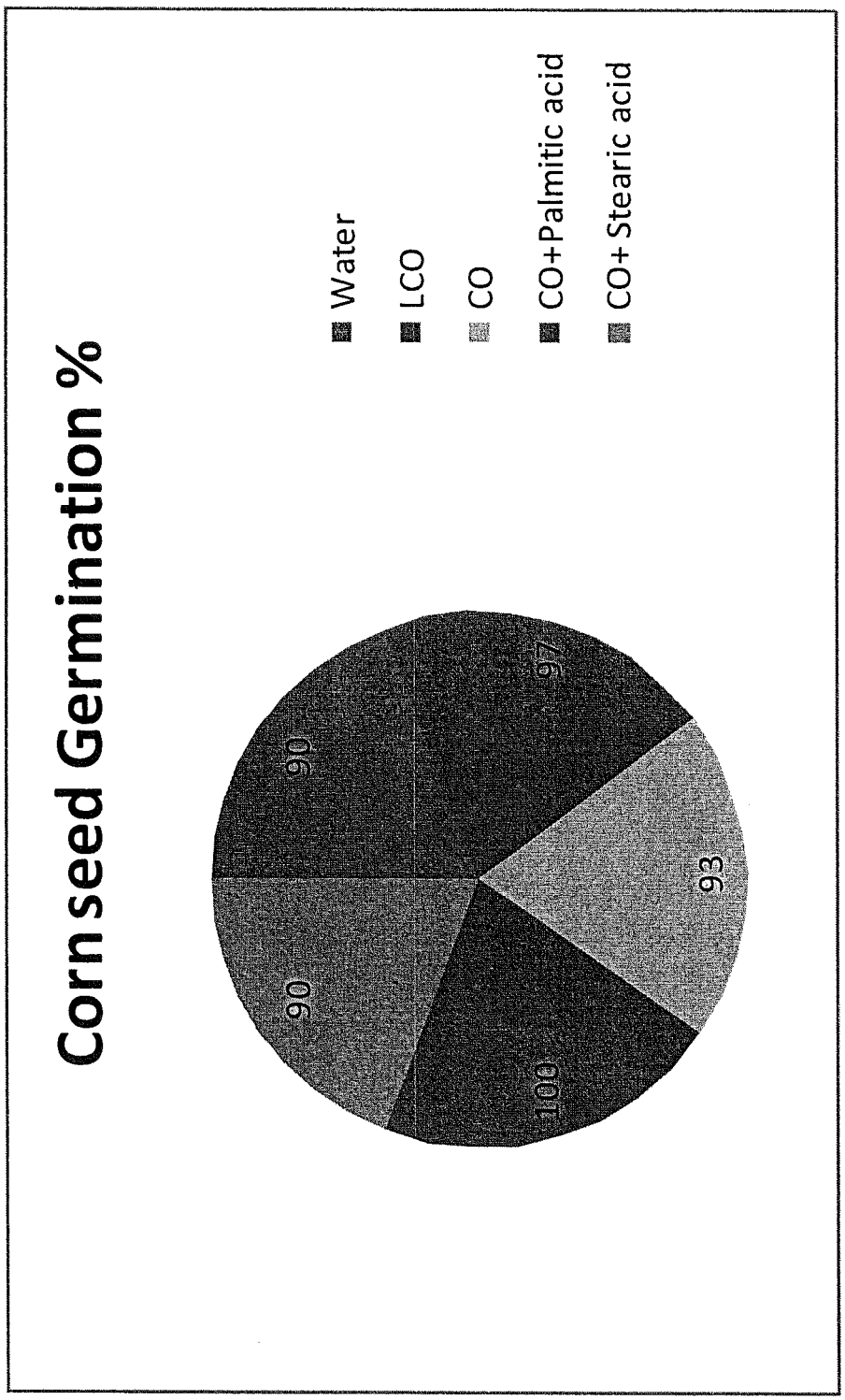
FIG. 7 is a pie-chart that illustrates the effect of the CO illustrated in FIG. 2a, alone or in combination with one of two different fatty acids, compared to the LCO illustrated in FIG. 2b, and water, treated on corn seed, expressed in terms of percent of seed germination.
Figure 8:
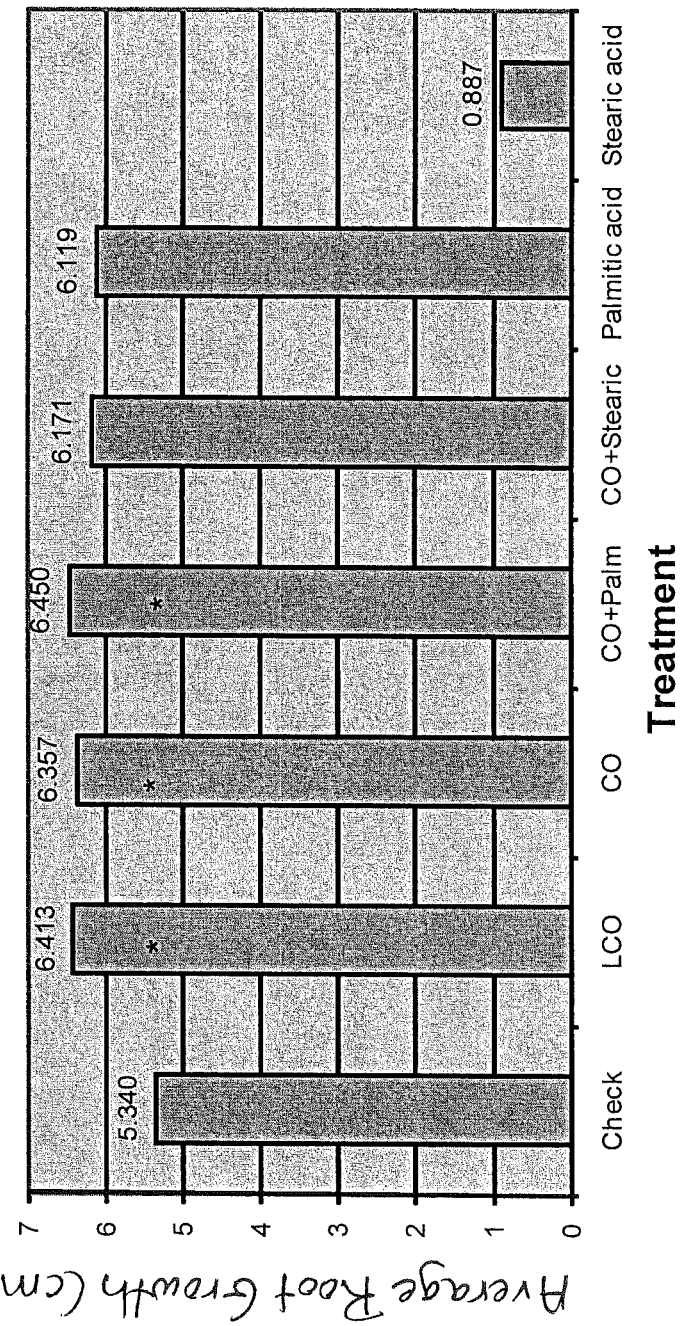
FIG. 8 is a graph that illustrates effect of the CO illustrated in FIG. 2a, alone or in combination with one of two different fatty acids, compared to the LCO illustrated in FIG. 2b, each of the fatty acids alone, and a control, treated on corn seed, expressed in terms of percent of seed germination.

In corn, Pea LCO, Pea CO and CO with Palmitic acid showed increased germination (FIG. 7) and they significantly increased seedling root length over control as well. Their effect was not statistically different, CO with Palmitic acid being the highest for germination and root length. Addition of Palmitic acid with CO seemed to be slightly beneficial (not statistically) over LCO or CO (FIG. 8).

Example 3

Corn Seed Application

Corn seeds were treated with various combinations of Pea CO (10-8 M) and Pea LCO (10-8, 10-9 M). Seeds were planted in greenhouse plastic pots containing 1:1 sand:perlite mixture. Seedlings were harvested 10 days after planting, washed clean and then dried in an oven at 60 C for 48 hr.

Figure 9:
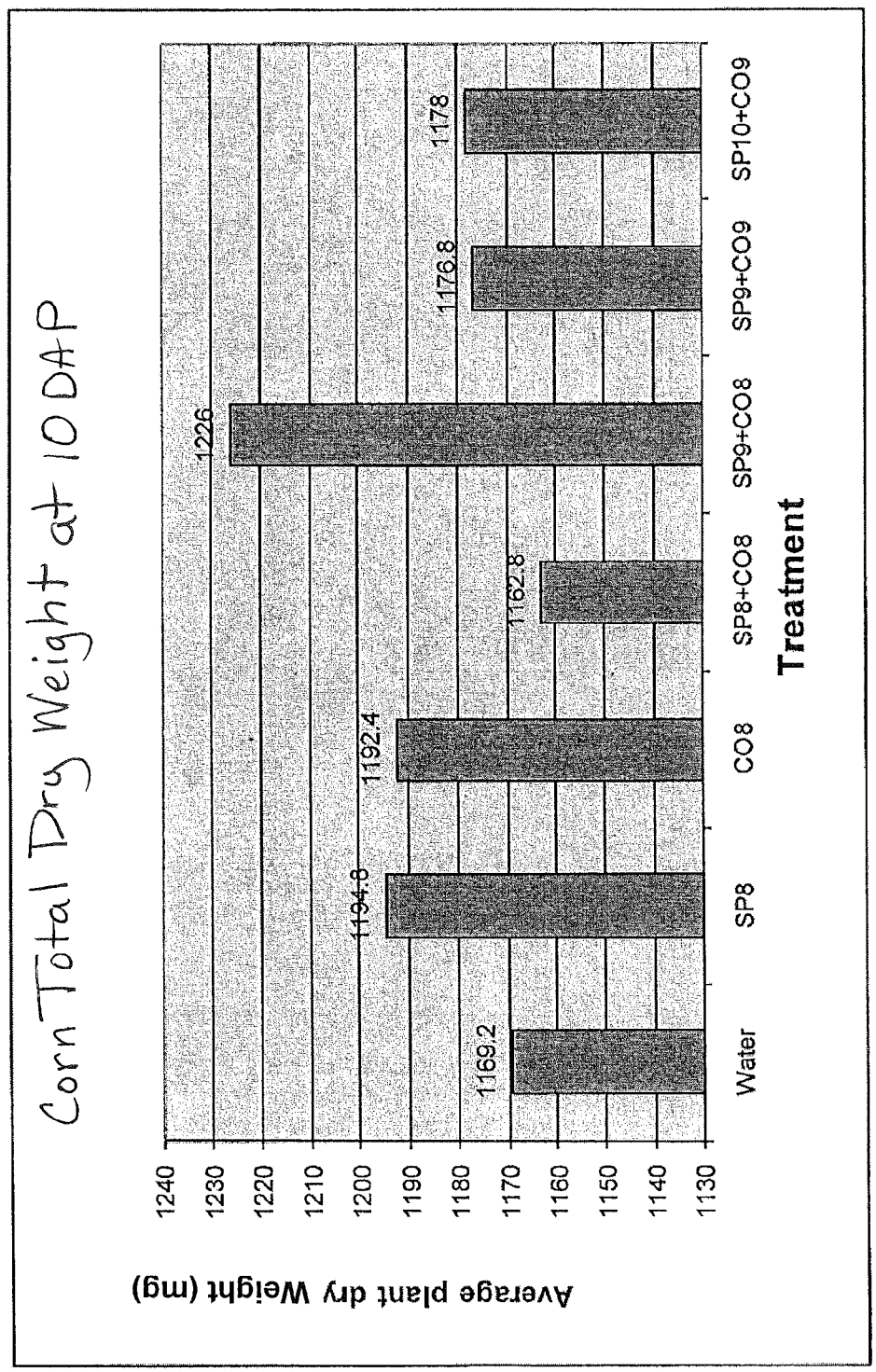
FIG. 9 is a bar graph that illustrates effect of the CO illustrated in FIG. 2a, alone or in combination with the LCO illustrated in FIG. 2b, compared to the LCO illustrated in FIG. 2b and water, treated on corn seed, expressed in terms of average plant dry weight.

As illustrated in FIG. 9, both CO ($10^{-8}$ M) (designated CO8) and LCO ($10^{-8}$ M)(designated SP8) alone increased corn seedling dry weight. Only the LCO at $10^{-9}$/CO at $10^{-8}$ combination increased corn seedling dry weight more than either Pea LCO (SP) or Pea CO.

Field Trials

Example 4

Corn

Sixteen (16) field trials were conducted to evaluate embodiments of the present invention on grain yield when applied to corn foliage. The field trials were conducted in eight states with various soil characteristics and environmental conditions.

The treatments used in the trials were Control (water), pure CO (chitooligosaccharide)—CO-V (illustrated in FIG. 2*a*) and pure LCO (lipo-chitooligosaccharide)—SP104 (illustrated in FIG. 2*b*). Different commercial corn hybrids were employed. Treatments were added to glyphosate herbicide and sprayed on the foliage at the time of normal herbicide application. Four ounces per acre of the treatments were combined with the herbicide, plus water and applied at a rate of 5 to 10 gallons per acre. Corn was grown to maturity, harvested and grain yield determined.

TABLE 1

| | YIELD (bu/A) | | |
| --- | --- | --- | --- |
| | Control | LCO (SP104) | CO (CO-V) |
| Mean (N = 16) | 192.6 | 196.8 | 201.8 |
| Response (bu/A) | | 4.2 | 9.2 |

TABLE 1-continued

| | YIELD (bu/A) | | |
|---|---|---|---|
| | Control | LCO (SP104) | CO (CO-V) |
| Response Increase (% of Control) | | 2.2 | 4.8 |
| Positive Yield Response (%) | | 75.0 | 93.8 |

As reflected by comparison between Control and CO, the yield was enhanced by foliar CO treatment by 9.2 bu/A, resulting in a 4.8% yield increase over Control, and a positive yield enhancement occurred in 93.8% of the trials.

In comparison to the foliar LCO response, the CO mean yield was 5.0 bu/A better, providing a 2.6% higher yield increase, and the trials with a positive response was 18.8% better.

Therefore, both CO and LCO provided yield enhancements as a foliar treatment, but the CO performed at least twice better than the LCO.

Example 5

Corn

Ten field trials were conducted to evaluate embodiments of the present invention on grain yield when applied to corn seed before planting. Five field trials were conducted in five states, and five trials were conducted in Argentina.

The treatments used in the trials were Control (water), pure CO (chitooligosaccharide)—CO-V (illustrated in FIG. 2a) and pure LCO (lipo-chitooligosaccharide)—SP104 (illustrated in FIG. 2b). CO and LCO treatments were 1×10-8 molar concentration resulting in 1 µg/acre applied. Different commercial corn hybrids were employed. Three fluid ounces of the treatment were applied to fifty (50) pounds of seed before planting. Corn was grown to maturity, harvested and grain yield determined.

The results are set forth in Table 2.

| | YIELD (bu/A) | | |
|---|---|---|---|
| | Control | LCO (SP104) | CO (CO-V) |
| Mean (N = 10) | 181.5 | 192.6 | 188.0 |
| Response (bu/A) | | 11.1 | 6.5 |
| Response Increase (% of Control) | | 6.1 | 3.6 |
| Positive Yield Response (%) | | 90.0 | 80.0 |

As reflected by comparison between Control and CO, the yield was enhanced by seed application of CO treatment by 6.5 bu/A, resulting in a 3.6% increase over the Control, and a positive yield enhancement occurred in 80.0% of the trials.

In comparison between CO and LCO, the CO mean yield was 4.6 bu/A less, resulting in 2.5% less yield increase above the Control, and 10.0% less positive yield responses amongst the ten trials.

Both the CO and LCO treatments provided yield enhancement above the Control when applied to corn seed, with the LCO providing the highest response.

All patent and non-patent publications cited in this specification are indicative of the level of skill of those skilled in the art to which this invention pertains. All these publications are herein incorporated by reference to the same extent as if each individual publication or patent application were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of enhancing corn plant growth, comprising treating a corn seed and/or a corn plant that germinates from the corn seed with an effective amount of at least one chitooligosaccharide (CO) and at least one lipo-chitooligosaccharide (LCO) represented by the following formula:

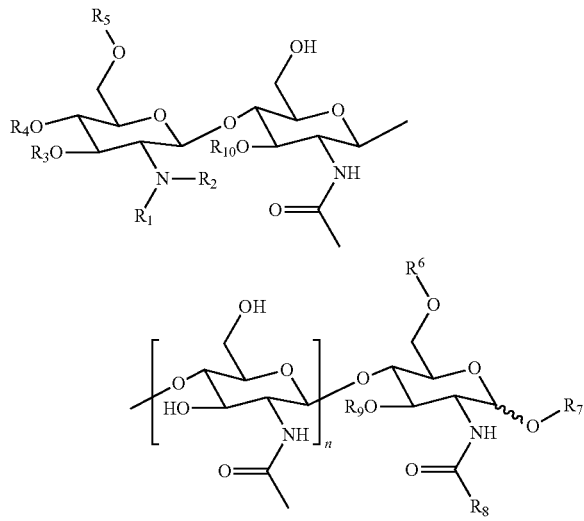

wherein $R_1$ represents C14:0, 3OH—C14:0, iso-C15:0, C16:0, 3-OH—C16:0, iso-C15:0, C16:1, C16:2, C16:3, iso-C17:0, iso-C17:1, C18:0, 3OH—C18:0, C18:0/3-OH, C18:1, OH—C18:1, C18:2, C18:3, C18:4, C19:1 carbamoyl, C20:0, C20:1, 3-OH—C20:1, C20:1/3-OH, C20:2, C20:3, C22:1, and C18-26(ω-1)-OH (which according to D'Haeze, et al., supra, includes C18, C20, C22, C24 and C26 hydroxylated species and C16:1Δ9, C16:2 (Δ2,9) and C16:3 (Δ2,4,9)); $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc, and 4-0-AcFuc; $R_7$ represents hydrogen, mannosyl or glycerol; $R_8$ represents hydrogen, methyl, or —CH$_2$OH; $R_9$ represents hydrogen, arabinosyl, or fucosyl; $R_{10}$ represents hydrogen, acetyl or fucosyl; and n represents 0, 1, 2 or 3, and wherein, upon harvesting, the corn plant exhibits at least one of increased plant yield measured in terms of bushels/acre, increased root number, increased root length, increased root mass, increased root volume and increased leaf area, compared to untreated plants and/or corn plants germinated from untreated corn seed.

2. The method of claim 1, wherein the at least one CO is represented by the formula:

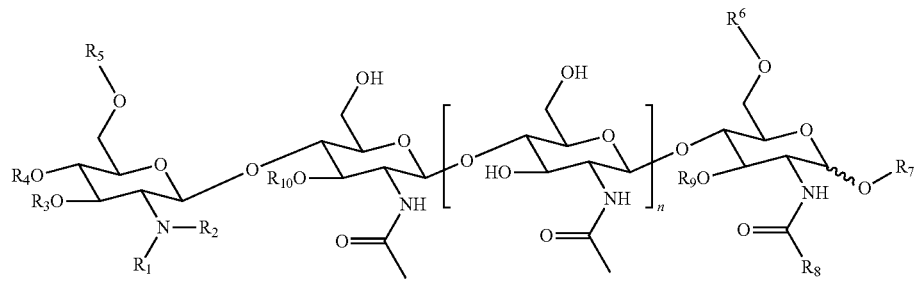

wherein $R_1$ and $R_2$ each independently represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc, and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3.

3. The method of claim 1, wherein the at least one CO comprises a CO represented by the structure:

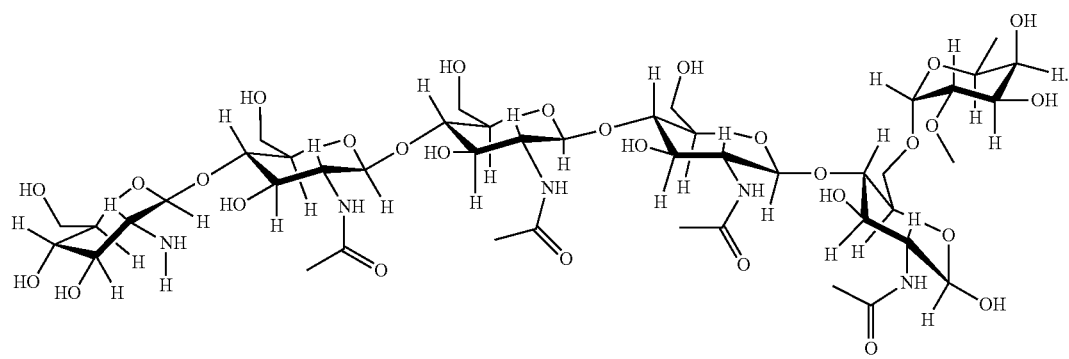

4. The method of claim 1, wherein the at least one CO comprises a CO represented by the structure:

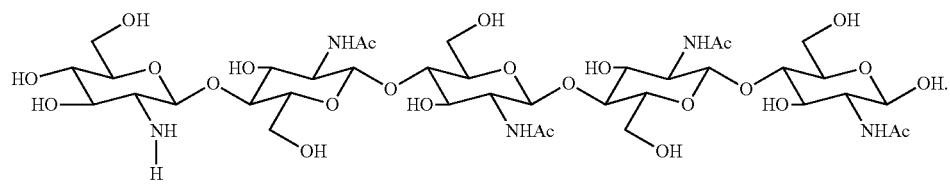 [SMILES: CC(=O)NC1C(O)OC(CO)C(OC2OC(CO)C(OC3OC(CO)C(OC4OC(CO)C(OC5OC(CO)C(O)C(O)C5N)C(O)C4NC(C)=O)C(O)C3NC(C)=O)C(O)C2NC(C)=O)C1O]

5. The method of claim 1, wherein the at least one CO comprises a CO represented by the formula:

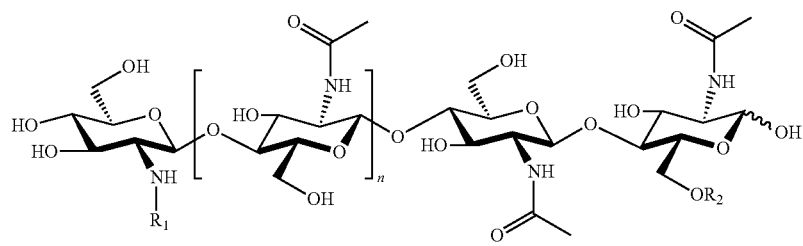

wherein n=1 or 2; $R_1$ represents hydrogen or methyl; and $R_2$ represents hydrogen or $SO_3H$.

6. The method of claim 1, wherein the at least one CO comprises a CO represented by the structure:

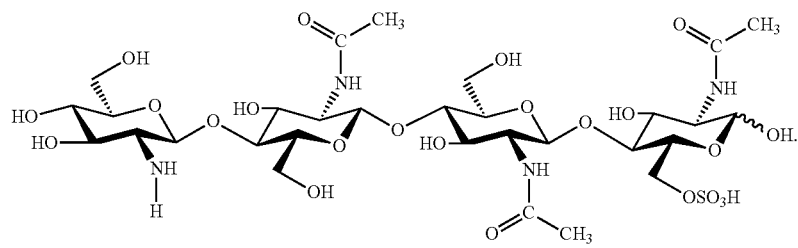

7. The method of claim 1, wherein the at least one CO comprises a CO represented by the structure:

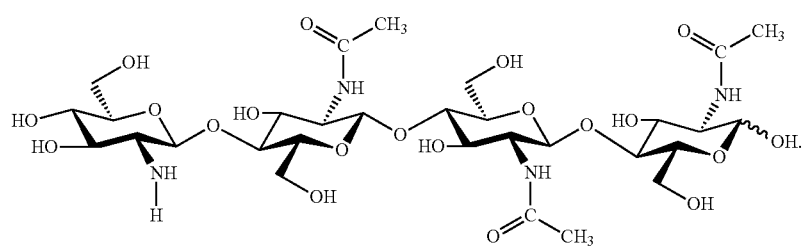

8. The method of claim 1, wherein the at least one CO comprises at least one synthetic CO.

9. The method of claim 1, wherein the at least one CO comprises at least one recombinant CO.

10. The method of claim 1, wherein the at least one CO and at least one LCO are applied to the corn seed prior to planting or at about the time of planting.

11. The method of claim 10, wherein the at least one CO is applied in an amount ranging from about $10^{-5}$ Molar to about $10^{-14}$ Molar.

12. The method of claim 1, wherein the at least one CO and at least one LCO are applied to the corn seed in furrow.

13. The method of claim 12, wherein the at least one CO is applied in an amount ranging from about 1 μg/acre to about 70 μg/acre.

14. The method of claim 1, wherein the at least one LCO comprises an LCO represented by the structure:

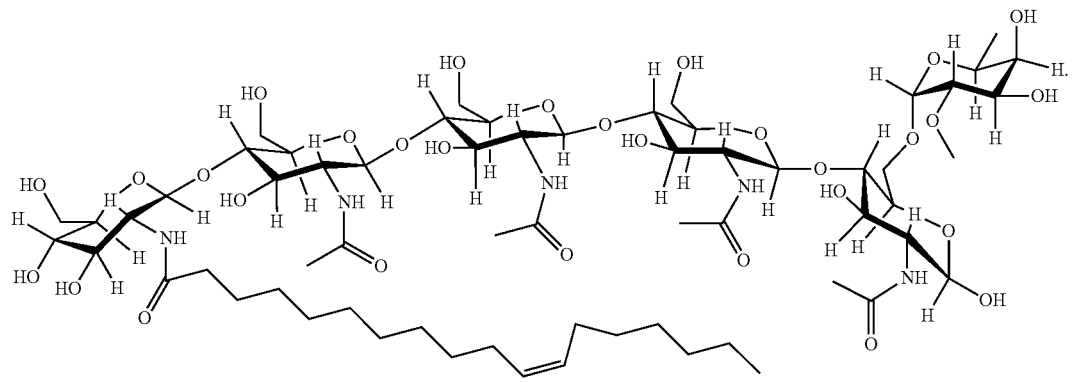

15. The method of claim 1, wherein the at least one LCO comprises an LCO represented by the structure:
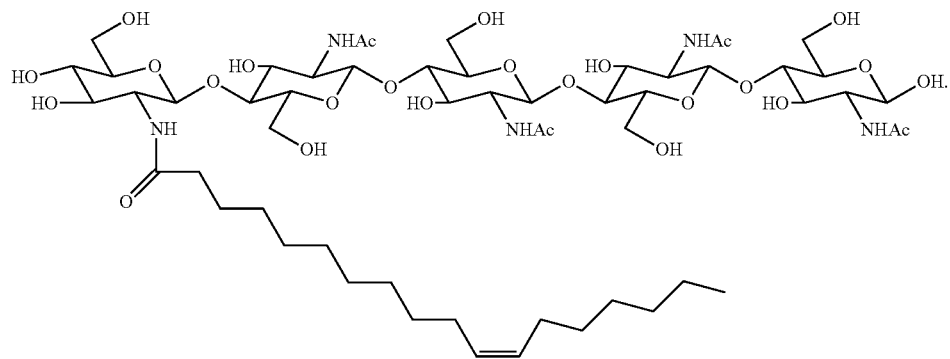 [SMILES: CCCCCC/C=C\CCCCCCCCCC(=O)NC1C(OC2C(CO)OC(OC3C(CO)OC(OC4C(CO)OC(OC5C(CO)OC(O)C(NC(C)=O)C5O)C(NC(C)=O)C4O)C(NC(C)=O)C3O)C(NC(C)=O)C2O)OC(CO)C(O)C1O]
16. The method of claim 1, wherein the at least one LCO comprises an LCO represented by the structure:
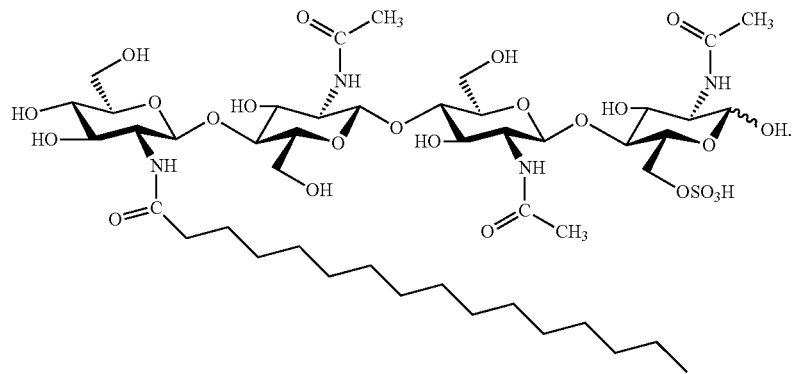
17. The method of claim 1, wherein the at least one LCO comprises an LCO represented by the structure:
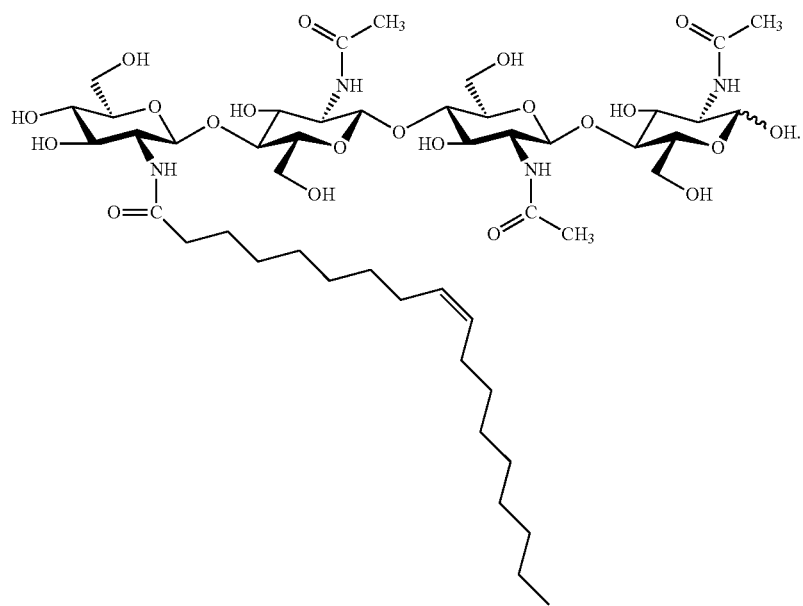

18. The method of claim 1, further comprising applying at least one micronutrient to the corn seed and/or to the corn plant that germinates from the corn seed.

19. The method of claim 18, wherein the micronutrient is selected from the group consisting of vitamins and trace minerals.

20. The method of claim 1, further comprising applying at least one fatty acid or fatty acid derivative to the corn seed and/or to the corn plant that germinates from the corn seed.

21. The method of claim 1, further comprising applying at least one plant signal molecule to the corn seed and/or to the corn plant that germinates from the corn seed.

22. The method of claim 21, wherein the at least one plant signal molecule comprises one or more of the following: chitinous compounds, flavonoids, jasmonic acid and derivatives thereof, linoleic acid and derivatives thereof, linolenic acid and derivatives thereof, and karrikins and derivatives thereof.

23. The method of claim 1, further comprising applying at least one herbicide, at least one insecticide, and/or at least one fungicide to the corn seed and/or to the corn plant that germinates from the corn seed.

24. The method of claim 1, further comprising applying at least one phosphate solubilising microorganism, at least one diazotroph (Rhizobial inoculants), and/or at least one mycorrhizal fungus to the corn seed and/or to the corn plant that germinates from the corn seed.

25. The method of claim 24, wherein the at least one phosphate solubilizing microorganism comprises a strain of the fungus *Penicillium*.

26. The method of claim 24, wherein the at least one phosphate solubilizing microorganism comprises a strain of *P. bilaiae*.

27. The method of claim 26, wherein the strain of *P. bilaiae* is selected from the group consisting of NRRL 50162, NRRL 50169, ATCC 20851, ATCC 22348, and ATCC 18309.

28. The method of claim 24, wherein the at least one phosphate solubilizing microorganism comprises a strain of *P. gaestrivorus*.

* * * * *